US006281409B1

(12) United States Patent
Woodhead et al.

(10) Patent No.: US 6,281,409 B1
(45) Date of Patent: Aug. 28, 2001

(54) BLACKCURRANT PROMOTERS AND GENES

(75) Inventors: Mary Rose Woodhead; Mark Andrew Taylor; Rex Michael Brennan, all of Dundee (GB)

(73) Assignee: SmithKline Beecham P.L.C., Brentford (GB)

( * ) Notice: Subject to any disclaimer, the term of this patent is extended or adjusted under 35 U.S.C. 154(b) by 0 days.

(21) Appl. No.: 09/068,140

(22) PCT Filed: Nov. 4, 1996

(86) PCT No.: PCT/EP96/04807

§ 371 Date: Nov. 2, 1998

§ 102(e) Date: Nov. 2, 1998

(87) PCT Pub. No.: WO97/17452

PCT Pub. Date: May 15, 1997

(30) Foreign Application Priority Data

Nov. 3, 1995 (GB) .................................................. 9522558

(51) Int. Cl.[7] .............................. C12N 5/04; C12N 15/29; C12N 15/82; A01H 5/00; A01H 5/10

(52) U.S. Cl. ..................... 800/287; 435/69.1; 435/320.1; 435/419; 435/468; 536/23.6; 536/24.1; 800/298

(58) Field of Search .................. 435/69.1, 320.1, 435/410, 419, 468, 6; 536/23.6, 24.1; 800/278, 287, 295, 298

(56) References Cited

FOREIGN PATENT DOCUMENTS

WO94/21794   9/1994  (WO) .............................. C12N/15/29

OTHER PUBLICATIONS

Graham et al., Plant Cell Tissue Organ Cult., vo.24, pp. 91–95 (1991).
Guarente et al, Trends Genet., vol. 8, pp. 27–32, 1992.*
Kim et al, Plant Mol. Biol, vol. 24, pp. 105–117, 1994.*
Kuntz et al, Plant J., vol. 13, pp. 351–361, 1998.*
Deruere et al, Biochem. Biophys. Res. Commun., vol. 199, pp. 1144–1150, 1994.*

* cited by examiner

Primary Examiner—Paula Hutzell
Assistant Examiner—Ashwin D. Mehta
(74) Attorney, Agent, or Firm—William R. Majarian; William T. King; Charles M. Kinzig

(57) ABSTRACT

Promoters capable of driving fruit-specific expression of DNA sequences in transgenic blackcurrant and other non-climacteric fruit are presented.

12 Claims, 11 Drawing Sheets

```
  1  CAGCATTCCA AGAGGAAAAA AAACATGATC AAGAAGTAAT TACTACAAAA
 51  GAGGAAGCTG TAGTAGTAAC TGCACCACCA CCATCAGAAA CAGCAGAGCC
101  AGCTGCAGCT GTTGTTGCCG AGGAAGAGAC AACAAAGGAG CAAGAAGAGC
151  CGCCAGCAGT ATCGGCCGAG GAACCTGTGG CCCCAGCTGA AGTAGAGACA
201  AAGGTGGAAG TTACAGAAGA ACCACCAAAA GTTGAGGAGA AACCAGCAGA
251  AGTAGAGGAG GCTCCAAAGG AAACAGTAGA AACAGAACCA GCTGTTGAGA
301  AGACCATCAA GGAGGAAACT GTAGAGGACT CTGTCGTGGC ACCTGCTCCC
351  GAACCGGAAG CCGAAGTCCC AAAAGAGAAG GTAATTGCTA CTACTGAAAC
401  TACTGAGGAA GAAGAAAAAG TGGCAGTTGA AGAAGTTGAA GTGAAAGTTG
451  AAACAGAGGA GGGAGAAGTT ACTGAGGAGA AGACTGAGTA AAATAAGTTG
501  TACAACTATT TTATGCACGC CTTATTTCT  CAATTGGAAG TTTATAATGT
551  AGTGGGCTTT TGGTAATATT TGGGGGTTTA ATAAGTGGTT TAAGTGGGTT
601  AAGGCTTTTT TGGAATTTAG ATATTTGGGT AAAGGCCTAC TTGAACAAAA
651  CATAGAAATT TGGCACACAT GGGTAAAAGT CAAACTTTGT TGAGGATGTT
701  TTCTTGTTGG TTAAATGTGT GTGCCAAGTA GTAGAATGTG GTGGTTGTAA
751  TGTAAGTTCT CAAGTAGGGT TTATGAGTCC TAGTATTATG CTTGATTGTA
801  TGTTGATATG AAAATGGGGG TATGTTGGCT TTGAATAAAA GTTTTTAATT
851  TTATAAAAAA AAAAAAAAAA AAAAAAAAAA AA
```

Figure 3

```
  1   AFQEEKKHDQ  EVITTKEEAV  VVTAPPPSET  AEPAAAVVAE  EETTKEQEEP

51   PAVSAEEPVA  PAEVETKVEV  TEEPPKVEEK  PAEVEEAPKE  TVETEPAVEK

101   TIKEETVEDS  VVAPAPEPEA  EVPKEKVIAT  TETTEEEEKV  AVEEVEVKVE

151   TEEGEVTEEK  TE
```

Figure 4

```
  1 AAACAACAAACTTTTTCATCAATCTTCTTTCTTTAATCATCACCATGTCGAGCTGCGGAA 60
      T  T  N  F  F  I  N  L  L  S  L  I  I  T  M  S  S  C  G  N

61 ACTGCGACTGTGCCGACAAGACCAACTGCCCAAAGAAGGGAAACAGCTACGGCTTTGACA 120
      C  D  C  A  D  K  T  N  C  P  K  K  G  N  S  Y  G  F  D  I

121 TCATTGAGACCCAGAAGAGCTACGATGACGTCGTGGTGATGGATGTTCAGGCAGCTGAGA 180
      I  E  T  Q  K  S  Y  D  D  V  V  V  M  D  V  Q  A  A  E  N

181 ATGATGGCAAGTGCAAGTGCGGCCCGAGCTGCAGTTGTGTGGGCTGCAGCTGTGGTCATT 240
      D  G  K  C  K  C  G  P  S  C  S  C  V  G  C  S  C  G  H  *

241 AAGTTAAACACAACATTATCATGTTATAGTGAATAATGATGTGTGTGATGAATATAGGTG 300
301 AAAAATCTGTGGTGTGATAAAAACCGTTGGTGAATAAATAGGTGTATATTTCGTGTGCAC 360
361 CTTCTACGAGTACTTGTGCTTGTTGGGTGAAAGAAATATGCACCTAAGTGTCAGTTGTTT 420
421 TCCGTGTTTTTCGCCGTGTCCCTTGTAATGGTCATGTTTGTGTTTTCTTGTGGTTAAATT 480
481 AAATGAACTAGTAATGTTATGTAAAAAAAAAAAAAAAA 519
```

Figure 5

```
  1 GGAGGAGATCACCAGTTCCACCAACACGTCGTCGTAATGAGACACGGCGATCGGATAGAC  60
    R  R  S  P  V  P  P  T  R  R  R  N  E  T  R  R  S  D  R  Q

61 AACTTCGAGCCACTGTGGGTGAAGACGGCGGCGAACGATGGGACCCACCCTTGGTCGATG 120
    L  R  A  T  V  G  E  D  G  G  E  R  W  D  P  P  L  V  D  E

121 AAGGCAAGCTCCGTACCTTCCGGACAGGTCTGAAGCTCCGAACCAATTTTGATTTTCCGA 180
    G  K  L  R  T  F  R  T  G  L  K  L  R  T  N  F  D  F  P  I

181 TCCATCGTGTCTTTGTATCACCTTTCCTCCGGTGCGTACAGACAGCATCGGAAGTCATCT 240
    H  R  V  F  V  S  P  F  L  R  C  V  Q  T  A  S  E  V  I  S

241 CCGCTCTCTGCGCCGTCGACGATATTCCCGCCACCACTAATAGAGGCGATCAAGTACAAA 300
    A  L  C  A  V  D  D  I  P  A  T  T  N  R  G  D  Q  V  Q  I

301 TCGATCCATCCAAGATCAAGGTCTCTATTGAGTATGGATTATGTGAAATGTTGAACATGC 360
    D  P  S  K  I  K  V  S  I  E  Y  G  L  C  E  M  L  N  M  Q

361 AAGCCATAAGACTTGGTATGGATTTCAGCAATGGGAATTGGGGTTTCGATAAATCACACC 420
    A  I  R  L  G  M  D  F  S  N  G  N  W  G  F  D  K  S  H  L

421 TTGAATCAACATTCCCAGTTGGGACGGTGGATCATAGTGTGGAACCACTCTATAAAGAGA 480
    E  S  T  F  P  V  G  T  V  D  H  S  V  E  P  L  Y  K  E  M

481 TGCCAAAATGGGAAGAGACAGTCAATGGCGCAAGGGCCAGATATGAAGAGGTTATTCAGG 540
    P  K  W  E  E  T  V  N  G  A  R  A  R  Y  E  E  V  I  Q  A

541 CCCTAGCAGATAAATACCCCACGGAGAACTTGTTGCTTGTTACACATGGGGAAGGAGTTG 600
    L  A  D  K  Y  P  T  E  N  L  L  L  V  T  H  G  E  G  V  G

601 GCGTTGCAGTTTCTGCCTTCATGAAGGATGTTACAGTGTACGAAGCCGATTATTGTGCCT 660
    V  A  V  S  A  F  M  K  D  V  T  V  Y  E  A  D  Y  C  A  Y

661 ATACACACGCAAGAAGATCCATTGTCTTGGGCAAAAACCAGTCATTTACTGCTGAAAACT 720
    T  H  A  R  R  S  I  V  L  G  K  N  Q  S  F  T  A  E  N  F

721 TTGAAGTATTACCAAAACAAGGCCAAACTGGTGTCAGTTACGTCCTTGAACAGCATTGAT 780
    E  V  L  P  K  Q  G  Q  T  G  V  S  Y  V  L  E  Q  H  *

781 GGAACTGTATGACCTAATTGTGGCAGCCGATGATTACAGAAACAATTTCCACACCTTTTT 840
841 TCTTTTTTCGGGCATTTGCCTACATTTTATAATTAATTAGGCATTCTCATAGCTAAGGCT 900
901 CATTGGATTCACATCCCTACTTGTTTAAAGGAGACTTTGATTTGTTGCCTCCAAACAGAA 960
961 CATATGTTGCTGTGTCCATCAGCTTTTTTTAACTGGGATTTCTATTTTTACAGTGTGTAA 1020
1021 AAAAAAAAAAAAAAAAAAAAAAAAAA 1046
```

Figure 6

```
  1 GTTGATGGCAGATGTGACCAACTCAGGAAAAATGCCAGGGTTGTTGCAATTGATTCTTAC  60
    V  D  G  R  C  D  Q  L  R  K  N  A  R  V  V  A  I  D  S  Y

61 GAAGATGTTCCTTTGAACGATGAGAACGCATTGAAAAAGGCAGTGGCTAGTCAGCCTGTG 120
    E  D  V  P  L  N  D  E  N  A  L  K  K  A  V  A  S  Q  P  V

121 CGCGTCGCCATTGAAGGAGGTGGCAGGGATTTCCAACTCTATCAATCAGGCGTCTTTACT 180
    R  V  A  I  E  G  G  G  R  D  F  Q  L  Y  Q  S  G  V  F  T

181 GGATCATGTGGGACGGCCCTAGACCATGGTGTGGCTGCTGTTGGGTATGGCACAGAAAAT 240
    G  S  C  G  T  A  L  D  H  G  V  A  A  V  G  Y  G  T  E  N

241 GGTGTGGATTACTGGATTGTAAGGAACTCATGGGGTGCAAGCTGGGGAGAGAGCGGCTAC 300
    G  V  D  Y  W  I  V  R  N  S  W  G  A  S  W  G  E  S  G  Y

301 ATCAGGATGGAACGTAATCTGGCAGGCACAGCTACGGGCAAATGTGGTATTGCAATGGAA 360
    I  R  M  E  R  N  L  A  G  T  A  T  G  K  C  G  I  A  M  E

361 GCCTCTTACCCTATTAAGAAAGGCCAAAATCCCCCAAACCCAGGACCATCTCCTCCATCT 420
    A  S  Y  P  I  K  K  G  Q  N  P  P  N  P  G  P  S  P  P  S

421 CCAATAAAGACCTCCAACAGTTTTGTGACAATTACTATACCTTGGCTGAAAGCACCACTT 480
    P  I  K  T  S  N  S  F  V  T  I  T  I  P  W  L  K  A  P  L

481 GCTGCTGTCTATTTGAGTTTGGCAGGTATTGCTTCGAGTGGGGATGTTGCCCACTCGAGG 540
    A  A  V  Y  L  S  L  A  G  I  A  S  S  G  D  V  A  H  S  R

541 CTGCCACTTGCTGTGATGACCATTACAGTTGCTGCCCACATGAGTATCCCATCTGCAACC 600
    L  P  L  A  V  M  T  I  T  V  A  A  H  M  S  I  P  S  A  T

601 TTAATGCAGGGACGTGTATGATGAGAAGGACAACCCATTGAGTGTGAAGGCATTGAAGCG 660
    L  M  Q  G  R  V  *

661 TACTCCCGCTAAACCTCATTGGGCCTTTGGGAACCGTGGCAAGAGCAGCAGTGCTTAAGA 720
721 ACATTGTGTCATCTATACAGTGAAAGTAAAACGAGGATGAAAAGTTGTATCAGGCAGGGC 780
781 TTGATGATCTCCTCGGTTTTATAGTACCGCATACCCTCATTCTCCATTAAGGTCATATAC 840
841 ATATGGACGGTTTATCAAAGTTTATTCAGATGCTAATTATGTATATATCATTTCTCAGTC 900
901 TCTGTATTTCATTTTAACGAGAACATAAACAGATCGTTATCAGCTACCAATTTCCACTGT 960
961 AAATCACGTTATCAATTATTTACTGGCCTCGCTGAAAAAAAAAAAAAAAAAAAAAA 1017
```

Figure 7

```
  1 CGGTTCAATCGCTGGATCAATCGAGCATATGGCGATGTATCCGGTTGATACGCTTAAAAC 60
     G  S  I  A  G  S  I  E  H  M  A  M  Y  P  V  D  T  L  K  T

61 TCGCATACAGGCTATTGGGTCATGTTCGGCTCAATCCGCCGGTCTCCGACAAGCCCTTGG 120
     R  I  Q  A  I  G  S  C  S  A  Q  S  A  G  L  R  Q  A  L  G

121 GTCGATACTGAAAGTTGAAGGTCCCGCCGGACTTTACCGTGGCATTGGTGCAATGGGTCT 180
     S  I  L  K  V  E  G  P  A  G  L  Y  R  G  I  G  A  M  G  L

181 CGGTGCAGGACCAGCTCACGCAGTGTATTTCTCCGTTTACGAGATGTGTAAGGAGACTTT 240
     G  A  G  P  A  H  A  V  Y  F  S  V  Y  E  M  C  K  E  T  F

241 TTCTCATGGTGATCCGAGCAATTCCGGTGCGCACGCCGTTTCGGGGGTGTTCGCGACGGT 300
     S  H  G  D  P  S  N  S  G  A  H  A  V  S  G  V  F  A  T  V

301 GGCAAGCGACGCGGTGATTACGCCGATGGATGTGGTGAAACAGAGGTTGCAGTTGCAGAG 360
     A  S  D  A  V  I  T  P  M  D  V  V  K  Q  R  L  Q  L  Q  S

361 CAGTCCGTACAAGGGTGTTGTTGATTGCGTGAGGAGGGTGTTGGTAGAAGAAGGGATTGG 420
     S  P  Y  K  G  V  V  D  C  V  R  R  V  L  V  E  E  G  I  G

421 CGCATTTTACGCATCTTATCGAACAACTGTGGTCATGAATGCCCCGTTTACGGCCGTTCA 480
     A  F  Y  A  S  Y  R  T  T  V  V  M  N  A  P  F  T  A  V  H

481 CTTCGCCACATATGAAGCCACGAAGAAAGGGTTGTTGGAGGTGTCGCCGGAGACTGCGAA 540
     F  A  T  Y  E  A  T  K  K  G  L  L  E  V  S  P  E  T  A  N

541 CGATGAGAATTTGTTAGTGCATGCTACTGCTGGTGCTGCTGCTGGAGCTTTGGCTGCAGT 600
     D  E  N  L  L  V  H  A  T  A  G  A  A  A  G  A  L  A  A  V

601 AGTAACCACTCCACTAGATGTTGTCAAAACTCAGTTGCAGTGCCAAGGTGTTTGCGGATG 660
     V  T  T  P  L  D  V  V  K  T  Q  L  Q  C  Q  G  V  C  G  C

661 CGACAGATTTTCTAGCAGTTCGATTCAGGATGTTATAGGAAGCATAGTGAAGAAAAATGG 720
     D  R  F  S  S  S  S  I  Q  D  V  I  G  S  I  V  K  K  N  G

721 ATATGTCGGGTTAATGAGGGGGTGGATTCCCAGAATGCTATTTCATGCTCCTGCTGCAGC 780
     Y  V  G  L  M  R  G  W  I  P  R  M  L  F  H  A  P  A  A  A

781 AATCTGCTGGTCTACTTATGAAGCCTCCAAAACATTCTTTCAAAAACTCAATGAGAGCAA 840
     I  C  W  S  T  Y  E  A  S  K  T  F  F  Q  K  L  N  E  S  N

841 TAGCAACAGCTCAGTTACCTAAGATTTCATATGTTTTTGTTGCTCTACTAGGCTTATCCA 900
     S  N  S  S  V  T  *

901 AAATCATGTCGATTGGTTTCACTTCACCACAGTTGCCATGAACAACTCAAAGCATCGAAT 960
 961 TTTACATGTATATTATGCAATCTAGATGCTTCTTGATATTTATTTTTATTTTTTCTTTTC 1020
1021 CAACTTTTGTAATTAGAATTAGCTACTATGGTTATGGCATGGAGTGTTTTATAATTGCTA 1080
1081 ATATCATCGTATAAGCAATGCTATTTGAGAAATTGTGGTGTAAGGTTAGAGTAATGTTAT 1140
1141 TTGCACAATCCACTTACATAGACCGCGGGACTCATTTAAAAAAAAAAAAAAAAAAA 1195
```

Figure 8

```
   1  GATCTTATAT TGGATGGTA AGTTTCAA TTACCTATA TGTAACTCTC AGCAAATCA AGCTTTTGAT GAAACCACA CAGAATATT
 101  ATGAATTTCT TTGACTCTTT GTCTCTGTAC CAAAATACGC ACACCACAAA AAATTCTTTT TGTATTATAT TCGTTTTTA TTTTTTAAC GTTTGGTAT
 201  TCAAACATCA TATAAGTAGG GGGGAATATT ATTGGACTC CTCCAAAAAC TTATACATT GTGATTACAC ATTTGAATGA CAGAAGTTTT TGATGAAGTG
 301  CCAATATCAA TCTTTTCTTA ATTGCTTCAT AAGGGTGTT TTTGTAATTA AAAGAAAGAT AAGGAAATTT AGCAAGAAGT GCATTATTGG GACTGGTATA
 401  TATGACAAGG ATCTGACGTG GCAAAGAAAG AAGTGGGTC CTGAGTCAGG TGTGTCCCAT CTGTCAATAT TCTTCAAAAG AGAGTCCACC ATCTCATAGA
 501  TGAGATTTAG AAAGTGGTTT CCACACAAAA ATATGACACA ACCCATCCAT GAACCAATAA AACATGACA GGTCATCATT TCTTTTCATT TTTTTCTC
 601  AAGATAATAA TACCTATTAG TGTCTTTAAC ACCGGCCTAA CTTTGCATTT GGTGACTTTT TATTGCCCAA TGTGGCTTG AAGGAAATAA
 701  AAAGGAAGT CTTTTCTTG ACCCCATATG GAAGAATTT CAATGAGAGA GATAGAGAGG AGGGATGGAG ATTGGGGTGG AGAATTGATA CGGATCTTCT
 801  TTAATTGGTA TATGTAAATC ACTCAGAAAC ACGTATACCA TATATGCATC AATGTCAATG TCACAGAAAA CGTAACTCAC GAACACATTT CGTAACATGC
 901  ATGCACCAAT CATACATTAT AACATAGTGT TACGACAATA AAAGATCTTT AGTCGTAAGA GCATTAGCTC CACCCACAAT GTTCAGTACG ATCGATAAT GTTTGACTTG
1001  CTAAGAAGG GTATATCTT TATTCATATA TCTACTTTTG ATATGACCTA AACCTTGTGT ATCGATAACG ATCGATAAT TATAAAACTT GAACAAAACA
1101  TGTGGGATGA GAAAATGTAT GAGACTGGCC ATTAGTTTTA GCCGGATGTG ATTGGGTAT AAATGTTAGA AATATCCGTTG AGTACCCCCA ATAATTTAAA ATCTCCAGCA
1201  ATTTCAAC AATTAAACT CCCCTTCAG ATGATAACT TCCAAACACC TTAACAAATG TAAAATTCGT TAGTAAGATT AAATTTGAAA TGATAACACA
1301  AATACTGTGA TTCCTTTTCT TCGAAGGGAA ATTCCTTCCT TCCAAACTGC ACAAAACACA CAAGCACACA TCCAAAGTA GTAGTATGAT TACACACATT TGAAAAAATG
1401  AGAGTGAATA AAGTCATGG TCACCTACTT ACCCAACTGC ACAAAACACA CAAGCACACA TCCAAAGTA GTAGTATGAT TACACACATT TGAAAAAATG
1501  ACCTCCATTA TTTTAGCCAC CTTCTCTGTA AAAAGAGTA CAAACAAATT ACTCCTATCA TTATTATAAA AATAGTAGCA TAACCTCATC TCCAATCCAC
1601  ACCATATATT TTACATTATT GCCAAACATG CTAAAACCTT CTTGTATTCA GTGAAAATGT GGTGCAAAT CCCAAGATTC TTCATGCC CTCTCTCTCT
1701  CTCTCTCT CTCTCCTC CCTCCTCCTC TCTCTCTC ATCAACTTGA GGGCTTTAGG ACCTTTGAGG ACCCTCTCT AAACCTCT CAATTGATCA TCTCTGC
                                                                                          ← Putative promoter sequence
```

Figure 9

```
  1 GATCTTATATTGAGGATGCAAAGTTTCAAATTACCTGATATGTAACTCTCAACAAAATCA   60
 61 AGCTTTTGATCATATAAATCGAAACCAACACACAATAATTATGAATTTCTTTGACTCTTT  120
121 GTCTCTGTACCAAAATACGCACACCACAAAAAATTCTTTTTGTATTATATTCGTTTTTTA  180
181 TTTTTTTAACGTTTTGGTATTCAAACATCATATAAGTAAGGGGGAATATTATTCGGACTC  240
241 CTCCAAAAACTTATGACATTGTGATTACACATTTGAATGACAGAAGTTTTTGATGAAGTG  300
301 CCAATATCAATCTTTTCTTAATTGCTTCATAAAGGGTGTTTTTGTAATTAAAAGAAAGAT  360
361 AAGGAAATTTAGCAAGAAGTGCATTATTGGGACTGGTATATATGACAAGGATCTGACGTG  420
421 GCAAAGAAAGAAAGTGGGTCCTGAGTCAGGTGTGTCCCATCTGTCAATATTCTTCAAAAG  480
481 AGAGTCCACCATCTCATAGATGAGATTTAGAAAGTGGTTTCCACAAAAAAATATGACACA  540
541 ACCCATCCATGAACCAATAAAAACATGACAGGTCATCATTTCTTTCTATTTTTTCTCTC   600
601 AAGATAATAATACCTATTAGTGTCTTTAACACCGGCCTAACTTTGCATTTCTTGTCATTT  660
661 GGTGACTTTTTATTGCCCAATTGTGGCTTGAAGGAAATAAAAAGGAAAGTCTTTTTCTTG  720
721 AACCCATATGGAAGCAATTTCAATGAGAGAGATAGAGAGGAGGGATGGAGATTGGGGTGG  780
781 AGAATTGATACGGATCTTCTTTAATTGGTATATGTAAATCACTCAGAAACACGTATACCA  840
841 TATATGCATCAATGTCAATGTCACAGAAAACGTAACTCACGAACACATTTCGTAACATGC  900
901 ATGCACCAATCATACATTATAACATAGTGTTACGACAATAAAAGATCTTTAGTCGTAAGA  960
961 GCATTAGCTCGTGACAAGAACAAAAACGTGGATTCCCAACCTAAAGAAGGGTATATCTTT 1020
1021 TATTCATATATCTACTTTTGATATGACCTAAACCTTGTGTCACCCACAATGTTCAGTACG 1080
1081 ATCGATAATTGTTTGACTTGTGTGGGATGAGAAAATGTATGAGACTGGCCATTAGTTTTA 1140
1141 GCCGGATGTGATTTGGGTATATTGATGACAATATAAGATATATAAAACTTGAACAAAACA 1200
1201 ATTTCTCAACAAATTAAACTACAAGATAATCTCCCTTCAGATGATAAACTAAATGGTAGA 1260
1261 ATATCCGTTGAGTACCCCCAATAATTTAAAATCTCCAGCAAATACTGTGATTCCTTTTCT 1320
1321 TCGAAGCGAAATTCCTTCCTTCCAAACACCTTAACAAATGTAAAATTCGTTAGTAAGATT 1380
1381 AAATTTGAAATGATAACACAAGAGTGAATAAAGGTCATGGTCACCTACTTACCCAACTGC 1440
1441 ACAAAACACAAGCACACATCCAAAAGTAGTAGTATGATTACACACATTTGAAAAAATG    1500
1501 ACCTCCATTATTTTAGCCACCTCTCTTGTAAAAAAGATTACAAACAAATTACTCCTATCA 1560
1561 TTATTATAAAAATAGTAGCATAACCTCATCTCCAATCCACACCATATATTTTACATTATT 1620
1621 GCCAAACATGCTAAAAGCTTCTTGTATTCAGTGAAAATGTGGTGTCAAATCCCAAGATTC 1680
1681 TTCATGTGCCCTCTCTCTCTCTCTCTCTCTCTCCTCCTCCTCCTCCTCTCTCTCTC     1740
1741 ATCAACTTGAGGGCTTTAGGACCTCTATATAAACCTCTCTCAATTGATCATCTCTGCATC 1800
1801 ACACTCTCAAGCATTCTTTCTCTACTTTCTTTAGGTCAACTACACTTCCCTTTGAGT    1860
1861 TTCCAATGGCCACTGTTGAGGTAAATCAAGTGATATATACATAAATTTATTTGAAAGAT  1920
         M  A  T  V  E
1921 GATTGATTCAAAGAGAACCCTTTTGTGTTTTCTTTAATAAGATCCATGTATATGAAGTTT 1980
1981 TAATGTTTCATGTTTTTTTATTTTTGTTAATTTTTTTTTAATTTAGGCATTTTTGCAAT  2040
2041 ATCCCATTTGTGAAAAGATCTGTTTTCCTTTGGAAGAGATTAGAATTCGTTTCGTGTCGA 2100
2101 TTCATCATGAAAATCAATCTGGGTCTAGCTTTAATTGTGCTGATCTTGACCGGACTGTTA 2160
2161 GATGATTCGTTTTATATGTAGGCCCAATAGAGAGTGATAGTATTCCCGAAATAATACAAA 2220
2221 TCCGAGCAAACTATAATCCTCAATAGTAACTTTGTAATCTCTAAATAATCAAAAAATAAT 2280
2281 GCTTATTGGGGTGATTGGTGTGTTTGATGCAGGTTGTATCAGCGCAGACAGCATTCCAAG 2340
                                   V  V  S  A  Q  T  A  F  Q  E
2341 AGGAAAAAAAACATGATCAAGAAGTAATTACTACAAAGAGGAAGCTGTAGTAGTAACTG  2400
       E  K  K  H  D  Q  E  V  I  T  T  K  E  A  V  V  V  T  A
2401 CACCACCACCATCAGAAACAGCAGAGCCAGCTGCAGCTGTTGTTGCCGAGGAAGAGACAA 2460
       P  P  P  S  E  T  A  E  P  A  A  V  V  A  E  E  T  T
2461 CAAAGGAGCAAGAAGAGCCGCCAGCAGTATCGGCCGAGGAACCTGTGGCCCCAGCTGAAG 2520
       K  E  Q  E  E  P  P  A  V  S  A  E  P  V  A  P  A  E  V
2521 TAGAGACAAAGGTGGAAGTTACAGAAGAACCACCAAAAGTTGAGGAGAAACCAGCAGAAG 2580
       E  T  K  V  E  V  T  E  E  P  P  K  V  E  E  K  P  A  E  V
2581 TAGAGGAGGCTCCAAAGGAAACAGTAGAAACAGAACCAGCTGTTGAGAAGACCATCAAGG 2640
       E  E  A  P  K  E  T  V  E  T  E  P  A  V  E  K  T  I  K  E
```

Figure 10 a

```
2641 AGGAAACTGTAGAGGACTCTGTCGTGGCACCTGCTCCCGAACCGGAAGCCGAAGTCCCAA 2700
      E  T  V  E  D  S  V  V  A  P  A  P  E  P  E  A  E  V  P  K
2701 AAGAGAAGGTAATTGCTACTACTGAAACTACTGAGGAAGAAGAAAAAGTGGCAGTTGAAG 2760
      E  K  V  I  A  T  T  E  T  T  E  E  E  K  V  A  V  E  E
2761 AAGTTGAAGTGAAAGTTGAAACAGAGGAGGGAGAAGTTACTGAGGAGAAGACTGAGTAAA 2820
      V  E  V  K  V  E  T  E  E  G  E  V  T  E  E  K  T  E  *
2821 ATAAGTTGTACAACTATTTTATGCACGCCTTATTTTCTCAATTGGAAGTTTATAATGTAG 2880
2881 TGGGCTTTTGGTAATATTTGGGGGTTTAATAAGTGGTTTAAGTGGGTTAAGGCTTTTTTG 2940
2941 GAATTTAGATATTTGGGTAAAGGCCTACTTGAACAAAACATAGAAATTTGGCACACATGG 3000
3001 GTAAAAGTCAAACTTTGTTGAGGATGTTTTCTTGTTGGTTAAATGTGTGTGCCAAGTAGT 3060
3061 AGAATGTGGTGGTTGTAATGTAAGTTCTCAAGTAGGGTTTATGAGTCCTAGTATTATGCT 3120
3121 TGATTGTATGTTGATATGAAAATGGGGGTATGTTGGCTTTGAATAAAAGTTTTTAATTTT 3180
3181 ATATAATAAGTGTATTTTTGTTTAATATCATTCTTTCATTCTCTCGGATCAACTACTGAT 3240
3241 CATCGCCTTGGTAAGCTATTGCCTCACCAACTAGCTAATCGAACGCGAGCCC         3292
```

Figure 10b

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
        (A) LENGTH: 882 base pairs
        (B) TYPE: nucleic acid
        (C) STRANDEDNESS: unknown
        (D) TOPOLOGY: unknown (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
        (A) ORGANISM: Ribes nigrum
        (B) STRAIN: Ben Alder (xi) SEQUENCE DESCRIPTION: SEQ ID NO: 1:

```
CAGCATTCCA AGAGGAAAAA AAACATGATC AAGAAGTAAT TACTACAAAA GAGGAAGCTG      60

TAGTAGTAAC TGCACCACCA CCATCAGAAA CAGCAGAGCC AGCTGCAGCT GTTGTTGCCG     120

AGGAAGAGAC AACAAAGGAG CAAGAAGAGC CGCCAGCAGT ATCGGCCGAG GAACCTGTGG     180

CCCCAGCTGA AGTAGAGACA AAGGTGGAAG TTACAGAAGA ACCACCAAAA GTTGAGGAGA     240

AACCAGCAGA AGTAGAGGAG GCTCCAAAGG AAACAGTAGA AACAGAACCA GCTGTTGAGA     300

AGACCATCAA GGAGGAAACT GTAGAGGACT CTGTCGTGGC ACCTGCTCCC GAACCGGAAG     360

CCGAAGTCCC AAAAGAGAAG GTAATTGCTA CTACTGAAAC TACTGAGGAA GAAGAAAAAG     420

TGGCAGTTGA AGAAGTTGAA GTGAAAGTTG AAACAGAGGA GGGAGAAGTT ACTGAGGAGA     480

AGACTGAGTA AAATAAGTTG TACAACTATT TTATGCACGC CTTATTTTCT CAATTGGAAG     540

TTTATAATGT AGTGGGCTTT TGGTAATATT TGGGGGTTTA ATAAGTGGTT TAAGTGGGTT     600

AAGGCTTTTT TGGAATTTAG ATATTTGGGT AAAGGCCTAC TTGAACAAAA CATAGAAATT     660

TGGCACACAT GGGTAAAAGT CAAACTTTGT TGAGGATGTT TTCTTGTTGG TTAAATGTGT     720

GTGCCAAGTA GTAGAATGTG GTGGTTGTAA TGTAAGTTCT CAAGTAGGGT TTATGAGTCC     780

TAGTATTATG CTTGATTGTA TGTTGATATG AAAATGGGGG TATGTTGGCT TTGAATAAAA     840

GTTTTTAATT TTATAAAAAA AAAAAAAAAA AAAAAAAAAA AA                       882
```

(2) INFORMATION FOR SEQ ID NO: 2:

(i) SEQUENCE CHARACTERISTICS:
        (A) LENGTH: 162 amino acids
        (B) TYPE: amino acid
        (C) STRANDEDNESS: unknown
        (D) TOPOLOGY: unknown (ii) MOLECULE TYPE: peptide (iii) HYPOTHETICAL: YES (iv) ANTI-SENSE: NO (v) FRAGMENT TYPE: N-terminal (vi) ORIGINAL SOURCE:
    (A) ORGANISM: Ribes nigrum
    (B) STRAIN: Ben Alder (xi) SEQUENCE DESCRIPTION: SEQ ID NO: 2:

```
Ala Phe Gln Glu Glu Lys Lys His Asp Gln Glu Val Ile Thr Thr Lys
1               5                   10                  15

Glu Glu Ala Val Val Thr Ala Pro Pro Ser Glu Thr Ala Glu
            20                  25                  30

Pro Ala Ala Ala Val Val Ala Glu Glu Thr Thr Lys Glu Gln Glu
            35                  40                  45

Glu Pro Pro Ala Val Ser Ala Glu Glu Pro Val Ala Pro Ala Glu Val
    50                  55                  60

Glu Thr Lys Val Glu Val Thr Glu Glu Pro Pro Lys Val Glu Glu Lys
65                  70                  75                  80

Pro Ala Glu Val Glu Glu Ala Pro Lys Glu Thr Val Glu Thr Glu Pro
                85                  90                  95

Ala Val Glu Lys Thr Ile Lys Glu Glu Thr Val Glu Asp Ser Val Val
            100                 105                 110

Ala Pro Ala Pro Glu Pro Glu Ala Glu Val Pro Lys Glu Lys Val Ile
            115                 120                 125

Ala Thr Thr Glu Thr Thr Glu Glu Glu Glu Lys Val Ala Val Glu Glu
            130                 135                 140

Val Glu Val Lys Val Glu Thr Glu Glu Gly Glu Val Thr Glu Glu Lys
145                 150                 155                 160

Thr Glu
```

(2) INFORMATION FOR SEQ ID NO: 3:

(i) SEQUENCE CHARACTERISTICS:
    (A) LENGTH: 519 base pairs
    (B) TYPE: nucleic acid
    (C) STRANDEDNESS: unknown
    (D) TOPOLOGY: unknown (ii) MOLECULE TYPE: cDNA (iii) HYPOTHETICAL: NO (iv) ANTI-SENSE: NO (vi) ORIGINAL SOURCE:
    (A) ORGANISM: Ribes nigrum
    (B) STRAIN: Ben Alder (xi) SEQUENCE DESCRIPTION: SEQ ID NO: 3:

```
AAACAACAAA CTTTTTCATC AATCTTCTTT CTTTAATCAT CACCATGTCG AGCTGCGGAA      60

ACTGCGACTG TGCCGACAAG ACCAACTGCC CAAAGAAGGG AAACAGCTAC GGCTTTGACA     120

TCATTGAGAC CCAGAAGAGC TACGATGACG TCGTGGTGAT GGATGTTCAG GCAGCTGAGA     180

ATGATGGCAA GTGCAAGTGC GGCCCGAGCT GCAGTTGTGT GGGCTGCAGC TGTGGTCATT     240

AAGTTAAACA CAACATTATC ATGTTATAGT GAATAATGAT GTGTGTGATG AATATAGGTG     300

AAAAATCTGT GGTGTGATAA AAACCGTTGG TGAATAAATA GGTGTATATT TCGTGTGCAC     360
```

```
CTTCTACGAG TACTTGTGCT TGTTGGGTGA AGAAATATG CACCTAAGTG TCAGTTGTTT      420

TCCGTGTTTT TCGCCGTGTC CCTTGTAATG GTCATGTTTG TGTTTTCTTG TGGTTAAATT      480

AAATGAACTA GTAATGTTAT GTAAAAAAAA AAAAAAAA                              519
```

(2) INFORMATION FOR SEQ ID NO: 4:

(i) SEQUENCE CHARACTERISTICS:
        (A) LENGTH: 65 amino acids
        (B) TYPE: amino acid
        (C) STRANDEDNESS: unknown
        (D) TOPOLOGY: unknown (ii) MOLECULE TYPE: peptide (iii) HYPOTHETICAL: YES (iv) ANTI-SENSE: NO (v) FRAGMENT TYPE: N-terminal (vi) ORIGINAL SOURCE:
        (A) ORGANISM: Ribes nigrum
        (B) STRAIN: Ben Alder (xi) SEQUENCE DESCRIPTION: SEQ ID NO: 4:

```
Met Ser Ser Cys Gly Asn Cys Asp Cys Ala Asp Lys Thr Asn Cys Pro
1               5                  10                  15

Lys Lys Gly Asn Ser Tyr Gly Phe Asp Ile Ile Glu Thr Gln Lys Ser
            20                  25                  30

Tyr Asp Val Val Val Met Asp Val Gln Ala Ala Glu Asn Asp Gly
        35                  40                  45

Lys Cys Lys Cys Gly Pro Ser Cys Ser Cys Val Gly Cys Ser Cys Gly
    50                  55                  60

His
65
```

(2) INFORMATION FOR SEQ ID NO: 5:

(i) SEQUENCE CHARACTERISTICS:
        (A) LENGTH: 1046 base pairs
        (B) TYPE: nucleic acid
        (C) STRANDEDNESS: unknown
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Ribes nigrum
        (B) STRAIN: Ben Alder (xi) SEQUENCE DESCRIPTION: SEQ ID NO: 5:

```
GGAGGAGATC ACCAGTTCCA CCAACACGTC GTCGTAATGA GACACGGCGA TCGGATAGAC       60

AACTTCGAGC CACTGTGGGT GAAGACGGCG GCGAACGATG GGACCCACCC TTGGTCGATG      120

AAGGCAAGCT CCGTACCTTC CGGACAGGTC TGAAGCTCCG AACCAATTTT GATTTTCCGA      180

TCCATCGTGT CTTTGTATCA CCTTTCCTCC GGTGCGTACA GACAGCATCG GAAGTCATCT      240

CCGCTCTCTG CGCCGTCGAC GATATTCCCG CCACCACTAA TAGAGGCGAT CAAGTACAAA      300

TCGATCCATC CAAGATCAAG GTCTCTATTG AGTATGGATT ATGTGAAATG TTGAACATGC      360

AAGCCATAAG ACTTGGTATG GATTTCAGCA ATGGGAATTG GGGTTTCGAT AAATCACACC      420
```

```
TTGAATCAAC ATTCCCAGTT GGGACGGTGG ATCATAGTGT GGAACCACTC TATAAAGAGA        480

TGCCAAAATG GGAAGAGACA GTCAATGGCG CAAGGGCCAG ATATGAAGAG GTTATTCAGG        540

CCCTAGCAGA TAAATACCCC ACGGAGAACT TGTTGCTTGT TACACATGGG AAGGAGTTG         600

GCGTTGCAGT TTCTGCCTTC ATGAAGGATG TTACAGTGTA CGAAGCCGAT TATTGTGCCT        660

ATACACACGC AAGAAGATCC ATTGTCTTGG GCAAAAACCA GTCATTTACT GCTGAAAACT        720

TTGAAGTATT ACCAAAACAA GGCCAAACTG GTGTCAGTTA CGTCCTTGAA CAGCATTGAT        780

GGAACTGTAT GACCTAATTG TGGCAGCCGA TGATTACAGA AACAATTTCC ACACCTTTTT        840

TCTTTTTTCG GGCATTTGCC TACATTTTAT AATTAATTAG GCATTCTCAT AGCTAAGGCT        900

CATTGGATTC ACATCCCTAC TTGTTTAAAG GAGACTTTGA TTTGTTGCCT CCAAACAGAA        960

CATATGTTGC TGTGTCCATC AGCTTTTTTT AACTGGGATT TCTATTTTTA CAGTGTGTAA       1020

AAAAAAAAAA AAAAAAAAA AAAAAA                                            1046
```

(2) INFORMATION FOR SEQ ID NO: 6:

(i) SEQUENCE CHARACTERISTICS:
        (A) LENGTH: 258 amino acids
        (B) TYPE: amino acid
        (C) STRANDEDNESS: unknown
        (D) TOPOLOGY: unknown (ii) MOLECULE TYPE: peptide (iii) HYPOTHETICAL: YES (iv) ANTI-SENSE: NO (v) FRAGMENT TYPE: N-terminal (vi) ORIGINAL SOURCE:
        (A) ORGANISM: Ribes nigrum
        (B) STRAIN: Ben Alder (xi) SEQUENCE DESCRIPTION: SEQ ID NO: 6:

```
Arg Arg Ser Pro Val Pro Pro Thr Arg Arg Asn Glu Thr Arg Arg
1               5                   10                  15

Ser Asp Arg Gln Leu Arg Ala Thr Val Gly Glu Asp Gly Glu Arg
            20                  25                  30

Trp Asp Pro Leu Val Asp Glu Gly Lys Leu Arg Thr Phe Arg Thr
        35                  40                  45

Gly Leu Lys Leu Arg Thr Asn Phe Asp Phe Pro Ile His Arg Val Phe
50                  55                  60

Val Ser Pro Phe Leu Arg Cys Val Gln Thr Ala Ser Glu Val Ile Ser
65                  70                  75                  80

Ala Leu Cys Ala Val Asp Asp Ile Pro Ala Thr Thr Asn Arg Gly Asp
                85                  90                  95

Gln Val Gln Ile Asp Pro Ser Lys Ile Lys Val Ser Ile Glu Tyr Gly
                100                 105                 110

Leu Cys Glu Met Leu Asn Met Gln Ala Ile Arg Leu Gly Met Asp Phe
            115                 120                 125

Ser Asn Gly Asn Trp Gly Phe Asp Lys Ser His Leu Glu Ser Thr Phe
130                 135                 140

Pro Val Gly Thr Val Asp His Ser Val Glu Pro Leu Tyr Lys Glu Met
145                 150                 155                 160

Pro Lys Trp Glu Glu Thr Val Asn Gly Ala Arg Ala Arg Tyr Glu Glu
                165                 170                 175
```

Val Ile Gln Ala Leu Ala Asp Lys Tyr Pro Thr Glu Asn Leu Leu Leu
            180                 185                 190

Val Thr His Gly Glu Gly Val Gly Val Ala Val Ser Ala Phe Met Lys
        195                 200                 205

Asp Val Thr Val Tyr Glu Ala Asp Tyr Cys Ala Tyr Thr His Ala Arg
    210                 215                 220

Arg Ser Ile Val Leu Gly Lys Asn Gln Ser Phe Thr Ala Glu Asn Phe
225                 230                 235                 240

Glu Val Leu Pro Lys Gln Gly Gln Thr Gly Val Ser Tyr Val Leu Glu
            245                 250                 255

Gln His (2) INFORMATION FOR SEQ ID NO: 7:

(i) SEQUENCE CHARACTERISTICS:
        (A) LENGTH: 1017 base pairs
        (B) TYPE: nucleic acid
        (C) STRANDEDNESS: unknown
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Ribes nigrum
        (B) STRAIN: Ben Alder (xi) SEQUENCE DESCRIPTION: SEQ ID NO: 7:

```
GTTGATGGCA GATGTGACCA ACTCAGGAAA AATGCCAGGG TTGTTGCAAT TGATTCTTAC      60

GAAGATGTTC CTTTGAACGA TGAGAACGCA TTGAAAAAGG CAGTGGCTAG TCAGCCTGTG     120

CGCGTCGCCA TTGAAGGAGG TGGCAGGGAT TTCCAACTCT ATCAATCAGG CGTCTTTACT     180

GGATCATGTG GGACGGCCCT AGACCATGGT GTGGCTGCTG TTGGGTATGG CACAGAAAAT     240

GGTGTGGATT ACTGGATTGT AAGGAACTCA TGGGGTGCAA GCTGGGGAGA GAGCGGCTAC     300

ATCAGGATGG AACGTAATCT GGCAGGCACA GCTACGGGCA AATGTGGTAT TGCAATGGAA     360

GCCTCTTACC CTATTAAGAA AGGCCAAAAT CCCCCAAACC CAGGACCATC TCCTCCATCT     420

CCAATAAAGA CCTCCAACAG TTTTGTGACA ATTACTATAC CTTGGCTGAA AGCACCACTT     480

GCTGCTGTCT ATTTGAGTTT GGCAGGTATT GCTTCGAGTG GGGATGTTGC CCACTCGAGG     540

CTGCCACTTG CTGTGATGAC CATTACAGTT GCTGCCCACA TGAGTATCCC ATCTGCAACC     600

TTAATGCAGG ACGTGTATG ATGAGAAGGA CAACCCATTG AGTGTGAAGG CATTGAAGCG     660

TACTCCCGCT AAACCTCATT GGGCCTTTGG GAACCGTGGC AAGAGCAGCA GTGCTTAAGA     720

ACATTGTGTC ATCTATACAG TGAAAGTAAA ACGAGGATGA AAAGTTGTAT CAGGCAGGGC     780

TTGATGATCT CCTCGGTTTT ATAGTACCGC ATACCCTCAT TCTCCATTAA GGTCATATAC     840

ATATGGACGG TTTATCAAAG TTTATTCAGA TGCTAATTAT GTATATATCA TTTCTCAGTC     900

TCTGTATTTC ATTTTAACGA GAACATAAAC AGATCGTTAT CAGCTACCAA TTTCCACTGT     960

AAATCACGTT ATCAATTATT TACTGGCCTC GCTGAAAAAA AAAAAAAAAA AAAAAAA      1017
```

(2) INFORMATION FOR SEQ ID NO: 8:

(i) SEQUENCE CHARACTERISTICS:
        (A) LENGTH: 206 amino acids
        (B) TYPE: amino acid
        (C) STRANDEDNESS: unknown (D) TOPOLOGY: unknown (ii) MOLECULE TYPE: peptide (iii) HYPOTHETICAL: YES (iv) ANTI-SENSE: NO (v) FRAGMENT TYPE: N-terminal (vi) ORIGINAL SOURCE:
        (A) ORGANISM: Ribes nigrum
        (B) STRAIN: Ben Alder (xi) SEQUENCE DESCRIPTION: SEQ ID NO: 8:

```
Val Asp Gly Arg Cys Asp Gln Leu Arg Lys Asn Ala Arg Val Val Ala
1               5                   10                  15

Ile Asp Ser Tyr Glu Asp Val Pro Leu Asn Asp Glu Asn Ala Leu Lys
            20                  25                  30

Lys Ala Val Ala Ser Gln Pro Val Arg Val Ala Ile Glu Gly Gly Gly
        35                  40                  45

Arg Asp Phe Gln Leu Tyr Gln Ser Gly Val Phe Thr Gly Ser Cys Gly
    50                  55                  60

Thr Ala Leu Asp His Gly Val Ala Val Gly Tyr Gly Thr Glu Asn
65                  70                  75                  80

Gly Val Asp Tyr Trp Ile Val Arg Asn Ser Trp Gly Ala Ser Trp Gly
                85                  90                  95

Glu Ser Gly Tyr Ile Arg Met Glu Arg Asn Leu Ala Gly Thr Ala Thr
                100                 105                 110

Gly Lys Cys Gly Ile Ala Met Glu Ala Ser Tyr Pro Ile Lys Lys Gly
            115                 120                 125

Gln Asn Pro Pro Asn Pro Gly Pro Ser Pro Pro Ser Pro Ile Lys Thr
        130                 135                 140

Ser Asn Ser Phe Val Thr Ile Thr Ile Pro Trp Leu Lys Ala Pro Leu
145                 150                 155                 160

Ala Ala Val Tyr Leu Ser Leu Ala Gly Ile Ala Ser Ser Gly Asp Val
                165                 170                 175

Ala His Ser Arg Leu Pro Leu Ala Val Met Thr Ile Thr Val Ala Ala
            180                 185                 190

His Met Ser Ile Pro Ser Ala Thr Leu Met Gln Gly Arg Val
            195                 200                 205
```

(2) INFORMATION FOR SEQ ID NO: 9:

(i) SEQUENCE CHARACTERISTICS:
        (A) LENGTH: 1311 base pairs
        (B) TYPE: nucleic acid
        (C) STRANDEDNESS: unknown
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Ribes nigrum
        (B) STRAIN: Ben Alder (xi) SEQUENCE DESCRIPTION: SEQ ID NO: 9:

```
GACGCCACTC ACCCTGAATT TCTCCACGTA CCAAAACCTA AACCTCATGA ATTCCACCCA      60

GAAATCTCTA TCGCGCCGTC GCATGATGGC CTTCAGTTCT GGCAGTTCAT GATCGCCGGT     120
```

```
TCAATCGCTG GATCAATCGA GCATATGGCG ATGTATCCGG TTGATACGCT TAAAACTCGC      180

ATACAGGCTA TTGGGTCATG TTCGGCTCAA TCCGCCGGTC TCCGACAAGC CCTTGGGTCG      240

ATACTGAAAG TTGAAGGTCC CGCCGGACTT TACCGTGGCA TTGGTGCAAT GGGTCTCGGT      300

GCAGGACCAG CTCACGCAGT GTATTTCTCC GTTTACGAGA TGTGTAAGGA GACTTTTTCT      360

CATGGTGATC CGAGCAATTC CGGTGCGCAC GCCGTTTCGG GGGTGTTCGC GACGGTGGCA      420

AGCGACGCGG TGATTACGCC GATGGATGTG GTGAAACAGA GGTTGCAGTT GCAGAGCAGT      480

CCGTACAAGG GTGTTGTTGA TTGCGTGAGG AGGGTGTTGG TAGAAGAAGG GATTGGCGCA      540

TTTTACGCAT CTTATCGAAC AACTGTGGTC ATGAATGCCC CGTTTACGGC CGTTCACTTC      600

GCCACATATG AAGCCACGAA GAAAGGGTTG TTGGAGGTGT CGCCGGAGAC TGCGAACGAT      660

GAGAATTTGT TAGTGCATGC TACTGCTGGT GCTGCTGCTG GAGCTTTGGC TGCAGTAGTA      720

ACCACTCCAC TAGATGTTGT CAAAACTCAG TTGCAGTGCC AAGGTGTTTG CGGATGCGAC      780

AGATTTTCTA GCAGTTCGAT TCAGGATGTT ATAGGAAGCA TAGTGAAGAA AAATGGATAT      840

GTCGGGTTAA TGAGGGGGTG GATTCCCAGA ATGCTATTTC ATGCTCCTGC TGCAGCAATC      900

TGCTGGTCTA CTTATGAAGC CTCCAAAACA TTCTTTCAAA AACTCAATGA GAGCAATAGC      960

AACAGCTCAG TTACCTAAGA TTTCATATGT TTTTGTTGCT CTACTAGGCT TATCCAAAAT     1020

CATGTCGATT GGTTTCACTT CACCACAGTT GCCATGAACA ACTCAAAGCA TCGAATTTTA     1080

CATGTATATT ATGCAATCTA GATGCTTCTT GATATTTATT TTTATTTTTT CTTTTCCAAC     1140

TTTTGTAATT AGAATTAGCT ACTATGGTTA TGGCATGGAG TGTTTTATAA TTGCTAATAT     1200

CATCGTATAA GCAATGCTAT TTGAGAAATT GTGGTGTAAG GTTAGAGTAA TGTTATTTGC     1260

ACAATCCACT TACATAGACC GCGGGACTCA TTTAAAAAAA AAAAAAAAA A              1311
```

(2) INFORMATION FOR SEQ ID NO: 10:

(i) SEQUENCE CHARACTERISTICS:
        (A) LENGTH: 289 amino acids
        (B) TYPE: amino acid
        (C) STRANDEDNESS: unknown
        (D) TOPOLOGY: unknown (ii) MOLECULE TYPE: peptide (iii) HYPOTHETICAL: YES (iv) ANTI-SENSE: NO (v) FRAGMENT TYPE: N-terminal (vi) ORIGINAL SOURCE:
        (A) ORGANISM: Ribes nigrum
        (B) STRAIN: Ben Alder (xi) SEQUENCE DESCRIPTION: SEQ ID NO: 10:

```
Met Ile Ala Gly Ser Ile Ala Gly Ser Ile Glu His Met Ala Met Tyr
1               5                  10                  15

Pro Val Asp Thr Leu Lys Thr Arg Ile Gln Ala Ile Gly Ser Cys Ser
            20                  25                  30

Ala Gln Ser Ala Gly Leu Arg Gln Ala Leu Gly Ser Ile Leu Lys Val
        35                  40                  45

Glu Gly Pro Ala Gly Leu Tyr Arg Gly Ile Gly Ala Met Gly Leu Gly
    50                  55                  60

Ala Gly Pro Ala His Ala Val Tyr Phe Ser Val Tyr Glu Met Cys Lys
65                  70                  75                  80
```

```
Glu Thr Phe Ser His Gly Asp Pro Ser Asn Ser Gly Ala His Ala Val
                 85                  90                  95

Ser Gly Val Phe Ala Thr Val Ala Ser Asp Ala Val Ile Thr Pro Met
            100                 105                 110

Asp Val Lys Gln Arg Leu Gln Leu Gln Ser Ser Pro Tyr Lys Gly
        115                 120                 125

Val Val Asp Cys Val Arg Arg Val Leu Val Glu Glu Gly Ile Gly Ala
    130                 135                 140

Phe Tyr Ala Ser Tyr Arg Thr Thr Val Val Met Asn Ala Pro Phe Thr
145                 150                 155                 160

Ala Val His Phe Ala Thr Tyr Glu Ala Thr Lys Lys Gly Leu Leu Glu
                165                 170                 175

Val Ser Pro Glu Thr Ala Asn Asp Glu Asn Leu Leu Val His Ala Thr
            180                 185                 190

Ala Gly Ala Ala Ala Gly Ala Leu Ala Ala Val Val Thr Thr Pro Leu
            195                 200                 205

Asp Val Val Lys Thr Gln Leu Gln Cys Gln Gly Val Cys Gly Cys Asp
    210                 215                 220

Arg Phe Ser Ser Ser Ser Ile Gln Asp Val Ile Gly Ser Ile Val Lys
225                 230                 235                 240

Lys Asn Gly Tyr Val Gly Leu Met Arg Gly Trp Ile Pro Arg Met Leu
                245                 250                 255

Phe His Ala Pro Ala Ala Ala Ile Cys Trp Ser Thr Tyr Glu Ala Ser
                260                 265                 270

Lys Thr Phe Phe Gln Lys Leu Asn Glu Ser Asn Ser Asn Ser Ser Val
            275                 280                 285

Thr
```

(2) INFORMATION FOR SEQ ID NO: 11:

(i) SEQUENCE CHARACTERISTICS:
        (A) LENGTH: 1797 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Ribes nigrum
        (B) STRAIN: Ben Alder (xi) SEQUENCE DESCRIPTION: SEQ ID NO: 11:

```
GATCTTATAT TGAGGATGCA AAGTTTCAAA TTACCTGATA TGTAACTCTC AACAAAATCA      60

AGCTTTTGAT CATATAAATC GAAACCAACA CACAATAATT ATGAATTTCT TTGACTCTTT     120

GTCTCTGTAC CAAAATACGC ACACCACAAA AAATTCTTTT TGTATTATAT TCGTTTTTTA     180

TTTTTTTAAC GTTTTGGTAT TCAAACATCA TATAAGTAAG GGGGAATATT ATTCGGACTC     240

CTCCAAAAAC TTATGACATT GTGATTACAC ATTTGAATGA CAGAAGTTTT TGATGAAGTG     300

CCAATATCAA TCTTTTCTTA ATTGCTTCAT AAAGGGTGTT TTTGTAATTA AAAGAAAGAT     360

AAGGAAATTT AGCAAGAAGT GCATTATTGG GACTGGTATA TATGACAAGG ATCTGACGTG     420

GCAAAGAAAG AAAGTGGGTC CTGAGTCAGG TGTGTCCCAT CTGTCAATAT TCTTCAAAAG     480

AGAGTCCACC ATCTCATAGA TGAGATTTAG AAAGTGGTTT CCACAAAAAA ATATGACACA     540
```

| | |
|---|---|
| ACCCATCCAT GAACCAATAA AAACATGACA GGTCATCATT TCTTTCTATT TTTTTCTCTC | 600 |
| AAGATAATAA TACCTATTAG TGTCTTTAAC ACCGGCCTAA CTTTGCATTT CTTGTCATTT | 660 |
| GGTGACTTTT TATTGCCCAA TTGTGGCTTG AAGGAAATAA AAAGGAAAGT CTTTTTCTTG | 720 |
| AACCCATATG GAAGCAATTT CAATGAGAGA GATAGAGAGG AGGGATGGAG ATTGGGGTGG | 780 |
| AGAATTGATA CGGATCTTCT TTAATTGGTA TATGTAAATC ACTCAGAAAC ACGTATACCA | 840 |
| TATATGCATC AATGTCAATG TCACAGAAAA CGTAACTCAC GAACACATTT CGTAACATGC | 900 |
| ATGCACCAAT CATACATTAT AACATAGTGT TACGACAATA AAAGATCTTT AGTCGTAAGA | 960 |
| GCATTAGCTC GTGACAAGAA CAAAAACGTG GATTCCCAAC CTAAAGAAGG GTATATCTTT | 1020 |
| TATTCATATA TCTACTTTTG ATATGACCTA AACCTTGTGT CACCCACAAT GTTCAGTACG | 1080 |
| ATCGATAATT GTTTGACTTG TGTGGGATGA GAAAATGTAT GAGACTGGCC ATTAGTTTTA | 1140 |
| GCCGGATGTG ATTTGGGTAT ATTGATGACA ATATAAGATA TATAAAACTT GAACAAAACA | 1200 |
| ATTTCTCAAC AAATTAAACT ACAAGATAAT CTCCCTTCAG ATGATAAACT AAATGGTAGA | 1260 |
| ATATCCGTTG AGTACCCCCA ATAATTTAAA ATCTCCAGCA AATACTGTGA TTCCTTTTCT | 1320 |
| TCGAAGCGAA ATTCCTTCCT TCCAAACACC TTAACAAATG TAAAATTCGT TAGTAAGATT | 1380 |
| AAATTTGAAA TGATAACACA AGAGTGAATA AAGGTCATGG TCACCTACTT ACCCAACTGC | 1440 |
| ACAAAACACA CAAGCACACA TCCAAAAGTA GTAGTATGAT TACACACATT TGAAAAAATG | 1500 |
| ACCTCCATTA TTTTAGCCAC CTCTCTTGTA AAAAAGATTA CAAACAAATT ACTCCTATCA | 1560 |
| TTATTATAAA AATAGTAGCA TAACCTCATC TCCAATCCAC ACCATATATT TTACATTATT | 1620 |
| GCCAAACATG CTAAAAGCTT CTTGTATTCA GTGAAAATGT GGTGTCAAAT CCCAAGATTC | 1680 |
| TTCATGTGCC CTCTCTCTCT CTCTCTCTCT CTCTCCTCCT CCTCCTCCTC TCTCTCTCTC | 1740 |
| ATCAACTTGA GGGCTTTAGG ACCTCTATAT AAACCTCTCT CAATTGATCA TCTCTGC | 1797 |

(2) INFORMATION FOR SEQ ID NO: 12:

(i) SEQUENCE CHARACTERISTICS:
        (A) LENGTH: 3292 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Ribes nigrum
        (B) STRAIN: Ben Alder (xi) SEQUENCE DESCRIPTION: SEQ ID NO: 12:

| | |
|---|---|
| GATCTTATAT TGAGGATGCA AAGTTTCAAA TTACCTGATA TGTAACTCTC AACAAAATCA | 60 |
| AGCTTTTGAT CATATAAATC GAAACCAACA CACAATAATT ATGAATTTCT TTGACTCTTT | 120 |
| GTCTCTGTAC CAAAATACGC ACACCACAAA AAATTCTTTT TGTATTATAT TCGTTTTTTA | 180 |
| TTTTTTTAAC GTTTTGGTAT TCAAACATCA TATAAGTAAG GGGAATATT ATTCGGACTC | 240 |
| CTCCAAAAAC TTATGACATT GTGATTACAC ATTTGAATGA CAGAAGTTTT TGATGAAGTG | 300 |
| CCAATATCAA TCTTTTCTTA ATTGCTTCAT AAAGGGTGTT TTTGTAATTA AAAGAAAGAT | 360 |
| AAGGAAATTT AGCAAGAAGT GCATTATTGG GACTGGTATA TATGACAAGG ATCTGACGTG | 420 |
| GCAAAGAAAG AAAGTGGGTC CTGAGTCAGG TGTGTCCCAT CTGTCAATAT TCTTCAAAAG | 480 |

-continued

| | | | | |
|---|---|---|---|---|
|AGAGTCCACC|ATCTCATAGA|TGAGATTTAG|AAAGTGGTTT|CCACAAAAAA ATATGACACA 540|
|ACCCATCCAT|GAACCAATAA|AAACATGACA|GGTCATCATT|TCTTTCTATT TTTTTCTCTC 600|
|AAGATAATAA|TACCTATTAG|TGTCTTTAAC|ACCGGCCTAA|CTTTGCATTT CTTGTCATTT 660|
|GGTGACTTTT|TATTGCCCAA|TTGTGGCTTG|AAGGAAATAA|AAAGGAAAGT CTTTTTCTTG 720|
|AACCCATATG|GAAGCAATTT|CAATGAGAGA|GATAGAGAGG|AGGGATGGAG ATTGGGGTGG 780|
|AGAATTGATA|CGGATCTTCT|TTAATTGGTA|TATGTAAATC|ACTCAGAAAC ACGTATACCA 840|
|TATATGCATC|AATGTCAATG|TCACAGAAAA|CGTAACTCAC|GAACACATTT CGTAACATGC 900|
|ATGCACCAAT|CATACATTAT|AACATAGTGT|TACGACAATA|AAAGATCTTT AGTCGTAAGA 960|
|GCATTAGCTC|GTGACAAGAA|CAAAAACGTG|GATTCCCAAC|CTAAAGAAGG GTATATCTTT 1020|
|TATTCATATA|TCTACTTTTG|ATATGACCTA|AACCTTGTGT|CACCCACAAT GTTCAGTACG 1080|
|ATCGATAATT|GTTTGACTTG|TGTGGGATGA|GAAAATGTAT|GAGACTGGCC ATTAGTTTTA 1140|
|GCCGGATGTG|ATTTGGGTAT|ATTGATGACA|ATATAAGATA|TATAAAACTT GAACAAAACA 1200|
|ATTTCTCAAC|AAATTAAACT|ACAAGATAAT|CTCCCTTCAG|ATGATAAACT AAATGGTAGA 1260|
|ATATCCGTTG|AGTACCCCCA|ATAATTTAAA|ATCTCCAGCA|AATACTGTGA TTCCTTTTCT 1320|
|TCGAAGCGAA|ATTCCTTCCT|TCCAAACACC|TTAACAAATG|TAAAATTCGT TAGTAAGATT 1380|
|AAATTTGAAA|TGATAACACA|AGAGTGAATA|AAGGTCATGG|TCACCTACTT ACCCAACTGC 1440|
|ACAAAACACA|CAAGCACACA|TCCAAAAGTA|GTAGTATGAT|TACACACATT TGAAAAAATG 1500|
|ACCTCCATTA|TTTTAGCCAC|CTCTCTTGTA|AAAAAGATTA|CAAACAAATT ACTCCTATCA 1560|
|TTATTATAAA|AATAGTAGCA|TAACCTCATC|TCCAATCCAC|ACCATATATT TTACATTATT 1620|
|GCCAAACATG|CTAAAAGCTT|CTTGTATTCA|GTGAAAATGT|GGTGTCAAAT CCCAAGATTC 1680|
|TTCATGTGCC|CTCTCTCTCT|CTCTCTCTCT|CTCCTCCT|CCTCCTCCTC TCTCTCTCTC 1740|
|ATCAACTTGA|GGGCTTTAGG|ACCTCTATAT|AAACCTCTCT|CAATTGATCA TCTCTGCATC 1800|
|ACACTCTCAA|GCATTCTTTC|TCTCTACTTT|CTTTTAGGTC|AACTACACTT CCCTTTGAGT 1860|
|TTCCAATGGC|CACTGTTGAG|GTAAATCAAG|TGATATATAC|ATAAATTTTA TTTGAAAGAT 1920|
|GATTGATTCA|AAGAGAACCC|TTTTGTGTTT|TCTTTAATAA|GATCCATGTA TATGAAGTTT 1980|
|TAATGTTTCA|TGTTTTTTTA|TTTTTTGTTA|ATTTTTTTTT|AATTTAGGCA TTTTTGCAAT 2040|
|ATCCCATTTG|TGAAAAGATC|TGTTTTCCTT|TGGAAGAGAT|TAGAATTCGT TTCGTGTCGA 2100|
|TTCATCATGA|AAATCAATCT|GGGTCTAGCT|TTAATTGTGC|TGATCTTGAC CGGACTGTTA 2160|
|GATGATTCGT|TTTATATGTA|GGCCCAATAG|AGAGTGATAG|TATTCCCGAA ATAATACAAA 2220|
|TCCGAGCAAA|CTATAATCCT|CAATAGTAAC|TTTGTAATCT|CTAAATAATC AAAAAATAAT 2280|
|GCTTATTGGG|GTGATTGGTG|TGTTTGATGC|AGGTTGTATC|AGCGCAGACA GCATTCCAAG 2340|
|AGGAAAAAAA|ACATGATCAA|GAAGTAATTA|CTACAAAAGA|GGAAGCTGTA GTAGTAACTG 2400|
|CACCACCACC|ATCAGAAACA|GCAGAGCCAG|CTGCAGCTGT|TGTTGCCGAG GAAGAGACAA 2460|
|CAAAGGAGCA|AGAAGAGCCG|CCAGCAGTAT|CGGCCGAGGA|ACCTGTGGCC CCAGCTGAAG 2520|
|TAGAGACAAA|GGTGGAAGTT|ACAGAAGAAC|CACCAAAAGT|TGAGGAGAAA CCAGCAGAAG 2580|
|TAGAGGAGGC|TCCAAAGGAA|ACAGTAGAAA|CAGAACCAGC|TGTTGAGAAG ACCATCAAGG 2640|
|AGGAAACTGT|AGAGGACTCT|GTCGTGGCAC|CTGCTCCCGA|ACCGGAAGCC GAAGTCCCAA 2700|
|AAGAGAAGGT|AATTGCTACT|ACTGAAACTA|CTGAGGAAGA|AGAAAAAGTG GCAGTTGAAG 2760|
|AAGTTGAAGT|GAAAGTTGAA|ACAGAGGAGG|GAGAAGTTAC TGAGGAGAAG ACTGAGTAAA 2820|

```
ATAAGTTGTA CAACTATTTT ATGCACGCCT TATTTTCTCA ATTGGAAGTT TATAATGTAG    2880

TGGGCTTTTG GTAATATTTG GGGGTTTAAT AAGTGGTTTA AGTGGGTTAA GGCTTTTTTG    2940

GAATTTAGAT ATTTGGGTAA AGGCCTACTT GAACAAAACA TAGAAATTTG GCACACATGG    3000

GTAAAAGTCA AACTTTGTTG AGGATGTTTT CTTGTTGGTT AAATGTGTGT GCCAAGTAGT    3060

AGAATGTGGT GGTTGTAATG TAAGTTCTCA AGTAGGGTTT ATGAGTCCTA GTATTATGCT    3120

TGATTGTATG TTGATATGAA AATGGGGGTA TGTTGGCTTT GAATAAAAGT TTTTAATTTT    3180

ATATAATAAG TGTATTTTTG TTTAATATCA TTCTTTCATT CTCTCGGATC AACTACTGAT    3240

CATCGCCTTG GTAAGCTATT GCCTCACCAA CTAGCTAATC GAACGCGAGC CC            3292
```

(2) INFORMATION FOR SEQ ID NO: 13:

(i) SEQUENCE CHARACTERISTICS:
        (A) LENGTH: 173 amino acids
        (B) TYPE: amino acid
        (C) STRANDEDNESS: unknown
        (D) TOPOLOGY: unknown (ii) MOLECULE TYPE: peptide (iii) HYPOTHETICAL: YES (iv) ANTI-SENSE: NO (v) FRAGMENT TYPE: N-terminal (vi) ORIGINAL SOURCE:
        (A) ORGANISM: Ribes nigrum
        (B) STRAIN: Ben Alder (xi) SEQUENCE DESCRIPTION: SEQ ID NO: 13:

```
Met Ala Thr Val Glu Val Val Ser Ala Gln Thr Ala Phe Gln Glu Glu
1               5                   10                  15

Lys Lys His Asp Gln Glu Val Ile Thr Thr Lys Glu Glu Ala Val Val
            20                  25                  30

Val Thr Ala Pro Pro Pro Ser Glu Thr Ala Glu Pro Ala Ala Ala Val
        35                  40                  45

Val Ala Glu Glu Glu Thr Thr Lys Glu Gln Glu Glu Pro Pro Ala Val
    50                  55                  60

Ser Ala Glu Glu Pro Val Ala Pro Ala Glu Val Glu Thr Lys Val Glu
65                  70                  75                  80

Val Thr Glu Glu Pro Pro Lys Val Glu Glu Lys Pro Ala Glu Val Glu
                85                  90                  95

Glu Ala Pro Lys Glu Thr Val Glu Thr Glu Pro Ala Val Glu Lys Thr
                100                 105                 110

Ile Lys Glu Glu Thr Val Glu Asp Ser Val Val Ala Pro Ala Pro Glu
            115                 120                 125

Pro Glu Ala Glu Val Pro Lys Glu Lys Val Ile Ala Thr Thr Glu Thr
        130                 135                 140

Thr Glu Glu Glu Lys Val Ala Val Glu Glu Val Glu Val Lys Val
145                 150                 155                 160

Glu Thr Glu Glu Gly Glu Val Thr Glu Glu Lys Thr Glu
                165                 170
```

(2) INFORMATION FOR SEQ ID NO: 14:

(i) SEQUENCE CHARACTERISTICS:
        (A) LENGTH: 5150 base pairs
        (B) TYPE: nucleic acid
        (C) STRANDEDNESS: unknown (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
    (A) ORGANISM: Ribes nigrum
    (B) STRAIN: Ben Alder (xi) SEQUENCE DESCRIPTION: SEQ ID NO: 14:

```
AGCTTATGAT TACAACTATA AAATCAATGC GTGGAAATCA CAAAAACTGG AAATGCTATG    60
CTATGGACGA TCAACTGATA AAACTGGAAA TAGGACTAAG AACTGTGAGA ACTAAACTAG   120
AGAAAACTTA ATGATCTAAA CTAAAAGTGA CAGCATTTTG GCAAATCTAA AAAGAGAGGT   180
TCATTGTCTG ATGATTGGTC CTTTCGTGCT TCCTCCTCCT TTGATTTTTA TAGGGCTTTC   240
ATCATTTAAT ATTACGATTG CCCAGCTGTC CATGATCCGG CCATAAATAG CCGGATATTC   300
TTGATTGGTA ATGGCTGTGC TTGATTGGCG GTATTTAACA CCTGCCGTTT TATTTGTAAA   360
AACCGTTATG GATTCTCTGA TGAGCATAAA CCACGCTGAA TCGGCCTATT GGTCGATTGG   420
TGTAAGGCCA TACTCTGAAC AGCCTTGGGG ATTCTGATGA CCGTAGATTC GGCCTTAATG   480
GGCATTATGA TCGTTACTTC GTCTCATGGT AACTCCATTT CGCAGTTTTA CCTATGGTGT   540
TCCTTGTCAT GAGTGTACCG GTCATTCCCA CTTCGTCAGA CACCTTTATC AGCCTAATCC   600
TAGGTCCATT AAAGTCTGGG GACCTGGATT TGTTATCCTC TAAATTAGAA AGACTATCCT   660
GATCATTTTT GTTCTTCGGT CATTAGCACC TAGGAGGTTT GGCCAGAAAC AGTCTCGTCC   720
TTTTGATCTT TCGGCCTCGC CAGGCCGGGT GGGTTTCCTG ATACAGAACT CGGCCTATAA   780
GCCGATTTAT ATGAGATGTA AACAGACACA AGATTGGTAA GTTATTTTCC ATGTCTAAGT   840
TCGACTCTCC GTGACCGTGA CCGTGACCGT TCTCCCTTTG CCCCAAATTG TTAGTTTAAC   900
AAAAATACTG GACAATTTCT CACTTGAGTA GTTATTCCCA ATTTTGTTTT CAAACTCTAT   960
CTGATGCAGC GGATTATGAA AGGTTAAGAA TTAAACAAGA ATATCACGTA TTCTCGTAAG  1020
AAGAAGAAGA ACACAGAGAA AAGTTCTCAG TTTTTATTGA TAAAATATGA ATAATAATCC  1080
CTAAAACAAC TTAGAAGTCT TGTTTAAATA GAAGCTAGCA AATCCTAATA TGAATAGGAA  1140
ACCCTAATAC GAAAATAAGA AATTACGATA AAAACTCAAC AGATAACGAA ATTACGAAAC  1200
TGTCTGAAAA CACTAAAAACT TAAATACAAG GTCCTTAATG ACGGAATTTG ACTAAAATCA  1260
CGAGACCATG TTACTTTTGT AACATGTCTT GAAGATCTCG ACGTTTCGCA CCAAGTCACC  1320
AAATTTCACA TAATTCCAAC ACTATTGCTA CTATTCACGA ACCCAAAATT CTCGCAAACA  1380
ACAGATTTAA CTTTACAGTC CAAGCTCCCT ACATCAGGCT CCCCTTCTTG AAAAGAACTC  1440
ATCCTCGATT TTCTTTCGAA AATTGAATTC TGCCTTCCCA TTGAAATAAA TACTTTGAAT  1500
ATACATTTTG CTTCAACCTT TTGGGCTCAA CAAAAATCAA CTTTTCTTCC ATCTCCAACT  1560
TTTGCACAAT ATCCAATAAT AAAGGATTAG AGAGAAAATT TCAACCCCA ATAAAATCAA   1620
TTTGTTGGAT CTCATTAAAT TGAATGAAAT CATGATTTTT TTGCTCAACA ATTTCTGATT  1680
TTATTTGCTT GATTTCTTCA TGCAACTCTT CTTGAGAACT ATCTTGCGTA ATAAAATCGC  1740
ATGTTTTCAT AGACTCAATG GAATCAAAAG TTTCTTCCTT CACTTCATTC AAATCATAAA  1800
CATATTCTTC AACTAAATCA ACATCTTGAT TTGATATGAT TTCTTCTACA ACTCCACCTT  1860
TATTTTGGTT GTCTTCGTTG ATCCCTTGGA TTTCACACAA AGTTGGTTCA TGGTCAACAA  1920
CATGTGCTCT CCACGAAATT CCATCACATG ATTGTTAATA TTTTGTTCTT TCACACTATA  1980
```

```
TTTATTTTCT AATATTTGTT CATAATTCCA CGGTAAAAAT TTACTTTCCA TGAGTTTCCT    2040

CATTCTTGAC CAACAACGAA TACGACGTTT ACCTTGATGT TCTCTTGATT CTTGTAATTT    2100

TAACCACCAC CATAACGCTG GACCTGCAAG TTTGCGTAAC ACATACCCCC ACTTCTCTTC    2160

TTCCGGAATA TTCATATGCT CAAAGAAATC TTCCATGTCC AATACCCAAT CAAGAAAATC    2220

TTCAAAGTAA ACACAACCGT TGAAACTAGG CATATTATTA TAATACCTAA AATCTCGACG    2280

AAGAGAAACA TAAACGTCAA CAAATCGATT AGCCGCTTGA ATCTCTTGAC GAAACTCCTG    2340

CCGGAGTTCC ATAAACTCTC CCACAGTCAC CACACTTCCC TCACGTTCAC CGTCCATGAG    2400

GATGGCTTTG ATACCAACTT GACGCAGCGG ATTATGAAAG GTTAAGAATT AAACAAGAAT    2460

AGCACGTATT CTCGTAAGAA GAAGAAGAAC ACGGAGAAAA GTTCTCAGTT TTTATTGATA    2520

AAATATGAAT AATAATCCCT GAAACAACTT AGAAGTCTTG TTTAAATAGA AGCTAGCAAA    2580

TCCTAATATG AATAGGAAAT CCTAATACGA AAATAAGAAA TTACGATAAA AACTCAACAA    2640

ATAACGAAAT TACGAAATTG TCTGAAAACA CTAAAACTTA AATACGAGGT CCTTAACGAC    2700

GGAATTTGAC TAAAATCACG AGACCATGTT ATGTAACATG TCTTGAAGAT CTCGACGTTT    2760

CGCACCAAGT CAACAAATTT CAACATAATT CCAATACTGT TACTACTATT CACGAACCCA    2820

AATTCTCGCA AACAACCGAT TTAACTTTAC CGTCCAAGCT CCATCATCA CTATCCAACA    2880

CAAAAATGAA AGAACATACA ATTTTACAAA CTTCATCTTT TCTTCTGATT CTTTCCTTCA    2940

CTTTAAAATA GAAAGAAAAA AGAAAACCAC ACTGATAGCT CCTTCCATTC CCATATCTCC    3000

CACTTGATTC TCAAAAACAC ATTTCTCCAA AATAATTGTG TATATGGCGA CAACAACCCA    3060

TGAAAGCGAT CTCCAATCTC CAATTATTCA CTCCTCCATC TCCATTTATA CATTAACCCC    3120

TCAACCTTAA CTCTTCACTT CCACACTCCA TTTTCATGGC GACCGACGCC ACTCACCCTG    3180

AATTTCTCCA CGTACCAAAA CCTAAACCTC ATGAATTCCA CCCAGAAATC TCTATCGCGC    3240

CGTCGCATGA TGGCCTTCAG TTCTGGCAGT TCATGATCGC CGGTTCAATC GCTGGATCAA    3300

TCGAGCATAT GGCGATGTAT CCGGTTGATA CGCTTAAAAC TCGCATACAG GGTATTGGGT    3360

CATGTTCGGC TCAATCCGCC GGTCTCCGAC AAGCCCTTGG GTCGATACTG AAAGTTGAAG    3420

GTCCCGCCGG ACTTTACCGT GGCATTGGTG CAATGGGTCT CGGTGCAGGA CCAGCTCACG    3480

CAGTGTATTT CTCCGTTTAC GAGATGTGTA AGGAGACTTT TTCTCATGGT GATCCGAGCA    3540

ATTCCGGTGC GCACGCCGTT TCGGGGGTGT TCGCGACGGT GGCAAGCGAC GCGGTGATTA    3600

CGCCGATGGA TGTGGTGAAA CAGAGGTTGC AGTTGCAGAG CAGTCCGTAC AAGGGTGTTG    3660

TTGATTGCGT GAGGAGGGTG TTGGTAGAAG AAGGGATTGG CGCATTTTAC GCATCTTATC    3720

GAACAACTGT GGTCATGAAT GCCCCGTTTA CGGCCGTTCA CTTCGCCACA TATGAAGCCA    3780

CGAAGAAAGG GTTGTTGGAG GTGTCGCCGG AGACTGCGAA CGATGAGAAT TTGTTAGTGC    3840

ATGCTACTGC TGGTGCTGCT GCTGGAGCTT TGGCTGCAGT AGTAACCACT CCACTAGATG    3900

TTGTCAAAAC TCAGTTGCAG TGCCAAGTAA GTCCCTTTTA ACTTTGCACT AAAAAAAAAA    3960

TAAGATTCAC TGTTCTAATT TCAGAATTAC ACCAATAAAA AAGGACAGAG CTAGCAATGA    4020

CTTGATTCTC TGAATTCGCA ATACGATAAT TCAGTATTGA TAGCTTATAG TATGTGGCCA    4080

AGCCAAGGCG TAGGATGAAT TTACCAGCCA GTTTGGAAGT TAATATCTTT TTTTGTATGG    4140

AGATATCGAT GAAGTTGGTG TGATTTTTGA AGTCACTAAA TGAGCTGCTA TCGCATGATA    4200

TATTGATGTG TAAAAATATT GAAAAGTGAA AAACGTTTCC AGAGAAACAA GCAACTCATC    4260

TTTATTCTTT AGAGATGGAG CTCGATTATG ATATGAACTT TGAAGCTTTG AATTGATCGA    4320
```

```
TGAAGCAACA AGACAAAATC TTTTATATTA AAAAAGTTGT CTTTCTGGTG GTTTATTCAG    4380

GGTGTTTGCG GATGCGACAG ATTTTCTAGC AGTTCGATTC AGGATGTTAT AGGAAGCATA    4440

GTGAAGAAAA ATGGATATGT CGGGTTAATG AGGGGGTGGA TTCCCAGAAT GCTATTTCAT    4500

GCTCCTGCTG CAGCAATCTG CTGGTCTACT TATGAAGCCT CCAAAACATT CTTTCAAAAA    4560

CTCAATGAGA GCAATAGCAA CAGCTCAGTT ACCTAAGATT TCATATGTTT TTGTTGTCTC    4620

TACTAGGCTT ATCCAAAATC ATGTCGATTG GTTTCACTTC ACCACAGTTG CCATGAACAA    4680

CTCAAAGCAT CGAATTTTAC ATGTATATTA TGCAATCTAG ATGCTTCTTG ATATTTATTT    4740

TTATTTTTTC TTTTCCAACT TTTGTAATTA GAATTAGCTA CTATGGTTAT GGCATGGAGT    4800

GTTTTATAAT TGCTAATATC ATCGTATAAG CAATGCTATT TGAGAAATTG TGGTGTAAGG    4860

TTAGAGTAAT GTTATTTGCC AATCCACTTA CATAGACCGC GGGACTCATT TATCATATGG    4920

ACCTACTTCT ATTTCTTATT AGGCAACTAG ATTCTACAAA TAACATTCTC CCGAAGGCTA    4980

TGTACAATGC ACCTTTTTTG AATTACAAAC TCTTCTGTTC AATATAAGAG GAATCTGGAA    5040

ATATCTGGTC CTAATTAACT ACAAGTCTAC AAGAATCATG TCATGCCATT AAGGTTCACT    5100

TCAAGTAAAG GTGAACACAA ATTAGGAGAA ATTTTAAATT AGAGACACTA              5150
```

(2) INFORMATION FOR SEQ ID NO: 15:

(i) SEQUENCE CHARACTERISTICS:
        (A) LENGTH: 328 amino acids
        (B) TYPE: amino acid
        (C) STRANDEDNESS: unknown
        (D) TOPOLOGY: unknown (ii) MOLECULE TYPE: peptide (iii) HYPOTHETICAL: YES (iv) ANTI-SENSE: NO (v) FRAGMENT TYPE: N-terminal (vi) ORIGINAL SOURCE:
        (A) ORGANISM: Ribes nigrum
        (B) STRAIN: Ben Alder (xi) SEQUENCE DESCRIPTION: SEQ ID NO: 15:

```
Met Ala Thr Asp Ala Thr His Pro Glu Phe Leu His Val Pro Lys Pro
1               5                   10                  15

Lys Pro His Glu Phe His Pro Glu Ile Ser Ile Ala Pro Ser His Asp
            20                  25                  30

Gly Leu Gln Phe Trp Gln Phe Met Ile Ala Gly Ser Ile Ala Gly Ser
        35                  40                  45

Ile Glu His Met Ala Met Tyr Pro Val Asp Thr Leu Lys Thr Arg Ile
 50                 55                  60

Gln Gly Ile Gly Ser Cys Ser Ala Gln Ser Ala Gly Leu Arg Gln Ala
65                  70                  75                  80

Leu Gly Ser Ile Leu Lys Val Glu Gly Pro Ala Gly Leu Tyr Arg Gly
                85                  90                  95

Ile Gly Ala Met Gly Leu Gly Ala Gly Pro Ala His Ala Val Tyr Phe
            100                 105                 110

Ser Val Tyr Glu Met Cys Lys Glu Thr Phe Ser His Gly Asp Pro Ser
        115                 120                 125

Asn Ser Gly Ala His Ala Val Ser Gly Val Phe Ala Thr Val Ala Ser
    130                 135                 140

Asp Ala Val Ile Thr Pro Met Asp Val Val Lys Gln Arg Leu Gln Leu
```

-continued

```
145                 150                 155                 160
Gln Ser Ser Pro Tyr Lys Gly Val Val Asp Cys Val Arg Arg Val Leu
            165                 170                 175
Val Glu Glu Gly Ile Gly Ala Phe Tyr Ala Ser Tyr Arg Thr Thr Val
            180                 185                 190
Val Met Asn Ala Pro Phe Thr Ala Val His Phe Ala Thr Tyr Glu Ala
            195                 200                 205
Thr Lys Lys Gly Leu Leu Glu Val Ser Pro Glu Thr Ala Asn Asp Glu
            210                 215                 220
Asn Leu Leu Val His Ala Thr Ala Gly Ala Ala Ala Gly Ala Leu Ala
225                 230                 235                 240
Ala Val Val Thr Thr Pro Leu Asp Val Val Lys Thr Gln Leu Gln Cys
            245                 250                 255
Gln Gly Val Cys Gly Cys Asp Arg Phe Ser Ser Ser Ser Ile Gln Asp
            260                 265                 270
Val Ile Gly Ser Ile Val Lys Lys Asn Gly Tyr Val Gly Leu Met Arg
            275                 280                 285
Gly Trp Ile Pro Arg Met Leu Phe His Ala Pro Ala Ala Ala Ile Cys
    290                 295                 300
Trp Ser Thr Tyr Glu Ala Ser Lys Thr Phe Phe Gln Lys Leu Asn Glu
305                 310                 315                 320
Ser Asn Ser Asn Ser Ser Val Thr
                325
```

BLACKCURRANT PROMOTERS AND GENES

The present invention relates to transgenic plant production and the expression of gene sequences introduced by genetic transformation procedures. In particular the present invention relates to blackcurrant (*Ribes nigrum* L.) fruit-specific gene promoters and their use in the expression of nucleic acid sequences in transgenic fruit.

Studies on the molecular basis of fruit ripening have concentrated on species whose fruit exhibit a climacteric pattern of ripening, for example tomato, avocado, apple, kiwifruit, peach and mango. Ripening in the fruit from these species is accompanied by a burst in the rate of respiration and a generally large increase in the rate of biosynthesis of the plant growth regulator, ethylene.

Non-climacteric fruit have a considerably different ripening mechanism. Examples of non-climacteric fruit are blueberry, cucumber, grape, orange and strawberry.

Fruit ripening is an important area of scientific research with particular attention being paid to high value fruits such as tomato, kiwifruit and avocado. In the tomato some of the genes involved in the ripening process have been isolated and characterised, for example the gene for polygalacturonase, an enzyme which acts on cell wall pectin. The level of expression of the polygalacturonase gene has been down-regulated in transgenic tomato fruit resulting in increased fruit firmness and consequently extended storage life (Schuch et al, 1991).

In contrast, less is known about the molecular basis of fruit ripening in non-climacteric fruit. In the work leading to the present invention we have found from measurements of respiration rate that blackcurrant fruit do not exhibit a respiratory climacteric during ripening and that ripe fruit produce very low levels of ethylene, hence blackcurrant can be classed as a non-climacteric fruit.

The blackcurrant is the most widely grown bush fruit in Europe, valued particularly for its high content of ascorbic acid and anthocyanin pigments. Areas for potential improvement in blackcurrants include enhancing pigment levels, aroma, flavour, texture, nutritional values (e.g. vitamin content), storage life, weather resistance, pest or pesticide resistance and manipulating sugar, soluble solids or acid levels in the fruit.

Plants with novel/improved characteristics can be produced by introducing genes or DNA sequences from the same or a different organism. Many examples are now in the literature of plant DNA sequences which have been used to drive the expression of foreign genes in plants. In most instances the regions adjacent to the 5' terminus of the coding regions of genes have been used in gene constructs. These regions are referred to as promoter sequences. In order to produce novel phenotypes it is necessary to have active expression of the introduced DNA sequence by cloning the sequence downstream of a promoter sequence active in plant tissue. These promoters may be derived from plant DNA or from other sources e.g. viruses. In most cases sequences up to 500–1000 bases are sufficient to allow for the regulated expression of foreign genes. However sequences longer than 1 kb may have useful features which permit high levels of gene expression in transgenic plants. Examples of fruit-specific promoters isolated from climacteric fruit such as tomato include the 2A11 promoter, and the polygalacturonase gene promoter.

Of considerable importance to the development of genetically improved blackcurrants is the finding in the work of the present invention that blackcurrant is in fact a non-climacteric fruit.

Promoters can vary in the level of expression and in the tissue-specific or developmental stage-specific pattern of expression that they drive. Some promoters are expressed in a tissue-specific or developmental stage-specific manner whereas others are expressed in each and every cell and are called constitutive promoters.

The most widely used constitutive promoters are the Cauliflower Mosaic Virus (CaMV) 35S promoter, nopaline synthetase (nos) and the octopine synthetase (ocs) promoters. Due to the different molecular mechanisms of ripening between climacteric and non-climacteric fruit it is hardly appropriate to use fruit-specific promoters isolated from climacteric fruit such as tomato (e.g. the 2A11 promoter or the polygalacturonase gene) in non-climacteric fruit.

Climacteric fruit-specific promoters therefore may not be suitable for many potential biotechnological applications for the improvement of non-climacteric fruit such as the blackcurrant which ideally require high levels of fruit-specific expression. In the case of the commonly used constitutive promoters, they have the disadvantage that they drive expression at high levels in all or nearly all cell types and throughout the development of the plant. Expression of the introduced gene or DNA sequence driven by a constitutive promoter can have a deleterious effect on normal plant development. Additionally, the commonly used constitutive promoters are derived from plant infectious agents such as plant viruses or Agrobacterium, a soil-borne infectious bacteria. The source of these promoters is a cause for concern in risk assessment of transgenic plant production.

SUMMARY OF THE INVENTION

Accordingly, the present invention provides promoters and a process for obtaining promoters capable of driving fruit-specific expression of DNA sequences in transgenic blackcurrant and other non-climacteric fruit. The process is as defined in claim 1 and the promoters as defined in claim 2. Preferably the promoter comprises the sequence of nucleic acid bases in FIG. 9 or IDSEQ 11 herein designated the RIBI promoter or in IDSEQ 14 herein designated the RIB 7 promoter. No previous promoters have been reported to be suitable to drive fruit-specific expression in blackcurrant and other non-climacteric fruit.

One advantage of the present invention is that because of the developmental stage specificity of the expression ie. it offers high level expression in fruit and only very low levels in other tissues, there is a reduced chance that the introduced DNA sequences will have an adverse effect on normal plant development.

The promoters of the present invention also have the advantage over some constitutive promoters in that they are naturally occurring plant gene sequences derived from blackcurrants, ie. a plant that is consumed by humans and not from plant pests or other infectious agents; this overcomes objections to the use of such sequences due to potential recombination.

DETAILED DESCRIPTION OF THE INVENTION

The isolation and characterisation of blackcurrant fruit-specific gene promoters and how they can be used to drive the expression of genes of interest in plants is given below and in the following examples. This description is purely for the purpose of illustrating the invention. It should be noted that the gene promoter may function in a similar (that is, fruit-specific) manner in other related species of non-climacteric fruit, in particular other Ribes species.

Promoters for use in the invention may be isolated from genomic libraries by the use of cDNA probes. The cDNA clones of genes highly expressed specifically in ripe blackcurrant fruit were obtained by differentially screening a cDNA library constructed from mRNA isolated from ripening blackcurrant fruit.

In a further aspect of the invention there is also provided cDNA for genes which exhibit differential expression in fruit during the ripening period of fruit development. In particular the cDNA is identified herein as pRIB1, pRIB3, pRIB5, pRIB6 and pRIB7.

The promoters of the present invention can be used to control the expression of one or more genes in non-climacteric and/or climacteric fruit. Preferably the non-climacteric fruit is the blackcurrant. Suitably the genes are novel/exogenous.

According to the present invention we also provide the use of promoters of the present invention in the transformation of plant cells to control the expression of one or more genes in non-climacteric/climacteric fruit.

In a further aspect of the invention there are provided novel plant cells and plants transformed using the promoter according to the present invention. Preferably the plants or seeds are blackcurrants.

According to the present invention, plant cells may be transformed using promoters of the invention using a variety of known transformation methods such as Agrobacterium-mediated or other vector-mediated transformation methods or physical transformation methods such as biolistics, chemical or electrical transfection or micro-injection.

In particular the RIB1 or RIB 7 promoter regions are suitable for incorporation into plasmid vectors designed for general use in construct production in *E. coli*, and for use in stable, Agrobacterium-mediated transformation (Bevan, 1984) and in transient transformation (Fromm et al., 1985) or stable, physical transformation methods (Klein et al., 1987). DNA sequences which one wishes to have expressed only in the fruit of transgenic blackcurrants and possibly other non-climacteric soft fruit can be inserted downstream of the promoter region of the blackcurrant RIB1 or RIB 7 gene, prior to introduction into plant cells or production of transgenic plants.

The transformed cells may then, in suitable cases, be regenerated into whole plants in which the new nuclear material is stably incorporated into the genome.

Examples of genetically modified plants according to the invention include as well as blackcurrants, fruits such as blueberry, cucumber, grape, orange and strawberry. Plants produced by the process of the invention may contain more than one recombinant gene. In order to prepare RNA suitable for a cDNA library construction, an improved method for the RNA extraction was developed as the available methods were found not to be applicable to blackcurrent fruit. The problems in working with blackcurrant tissue include the combination of the high levels of phenolic compounds and polysaccharides and the high acidity of berry extracts.

Accordingly in a further aspect of the present invention there is provided a method of extracting nucleic acid in particular RNA from blackcurrant fruit. One known method for grape berries (Tesniere & Vayda, 1991) was found to be unable to yield large quantities of good quality RNA from blackcurrant fruit which was not contaminated with coloured substances. This method was the basis for the modified method for the extraction of RNA from blackcurrant fruit.

Two key modifications were the method of tissue homogenisation and the inclusion of 8.5% (w/v) insoluble polyvinylpolypyrrolidone (PVPP) in the homogenisation buffer. The use of PVPP resulted in the removal of pigment from the fruit pulp at the start of the extraction procedure producing a clear final RNA pellet. Pulping fruit in the homogenisation buffer rather than grinding frozen fruit in a fine powder in liquid nitrogen and then adding the buffer was a less harsh method of tissue maceration and resulted in less disruption of cells and a reduction in the amount of gelatinous material. Pulping also reduced the problem of extracting large amounts of seed as well as fruit RNA which otherwise occurred during grinding in liquid nitrogen. Each fruit can frequently contain over twenty seeds and these are impossible to manually extract quickly enough to prevent the expression and subsequent isolation of wound-induced mRNA's from the fruit. In ripe fruit the problem can be solved using a juicerator (Acme). This macerates the fruit tissue to a pulp which can be collected and retains the seed and large pieces of skin material. Unripe fruit (i.e. green or green/red) were too hard to be pulped using this method so a coffee grinder was used instead.

The average yield of total RNA using this method is 15–20 μg RNA per g fresh weight of fruit, for each stage of ripening investigated. The ratio of $A_{260}/A_{280}$ nm was between 1.8–2.0. The yield was the same whether RNA was extracted from the pulp on the day of fruit harvest or whether the pulp was stored at −80° C., defrosted and subsequently used in an extraction. This implies that the RNA remains stable in the pulp. The yields are similar to those obtained from other fruit tissues e.g. apples (13 μg RNA per g fresh weight Lay-Yee et al., 1990) and peaches (12–15 μg RNA per g fresh weight, Callahan et al, 1989).

Denaturing agarose gel electrophoresis revealed that two ribosomal RNA bands were clearly visible suggesting that the RNA extracted using this new procedure was undegraded. In addition the RNA isolated from the fruit was capable of directing the synthesis of polypeptides as demonstrated by in vitro translation using a wheat germ lysate system. Polypeptides of up to approximately 80 kD were synthesised and the incorporation of $^{35}$S-methionine into TCA precipitable products was about 30 times higher than background values when 20 μg of total RNA were used compared with the minus RNA control.

The new extraction method described below in Example 2 allowed for the first time the extraction of RNA from blackcurrant fruit. This RNA has been shown to be biologically active, as demonstrated by in vitro translation results. In addition this RNA has been used to construct a cDNA library from an early ripening stage (Example 4 below). The cDNA library contained approx. 6.6×10$^6$ primary clones with an average insert size of 900 base pairs. Differential screening of 10,000 clones has resulted in the isolation of 5 clones which show an increase in expression during ripening.

The invention will be described further with reference to the following figures, in which;

BRIEF DESCRIPTION OF THE DRAWINGS

FIG. 3 shows the nucleotide sequence of the pRIB1 cDNA clone (IDSEQ 1).;

FIG. 4 shows the deduced amino acid sequence encoded by pRIB1 (IDSEQ 2);

FIG. 5 shows the nucleotide and predicted amino acid sequence of pRIB3 (IDSEQ 3 and 4 respectively);

FIG. 6 shows the nucleotide and predicted amino acid sequence of pRIB 5 (IDSEQ 5 and 6 respectively);

FIG. 7 shows the nucleotide and predicted amino acid sequence of pRIB 6 (IDSEQ 7 and 8 respectively);

FIG. 8 shows the nucleotide and predicted amino acid sequence of pRIB 7 (IDSEQ 9 and 10 respectively);

FIG. 9 shows the nucleotide sequence of the RIB1 promoter up to the transcription start site (IDSEQ 11), and FIGS. 10a–10b shows the RIBI gene sequence (IDSEQ 12) and the deduced amino acid sequence (IDSEQ 13). The transcription start site was located by primer extension analysis and this C residue in position 1797 is indicated in bold type and underlined in the figure.

EXAMPLES

Figure 1:
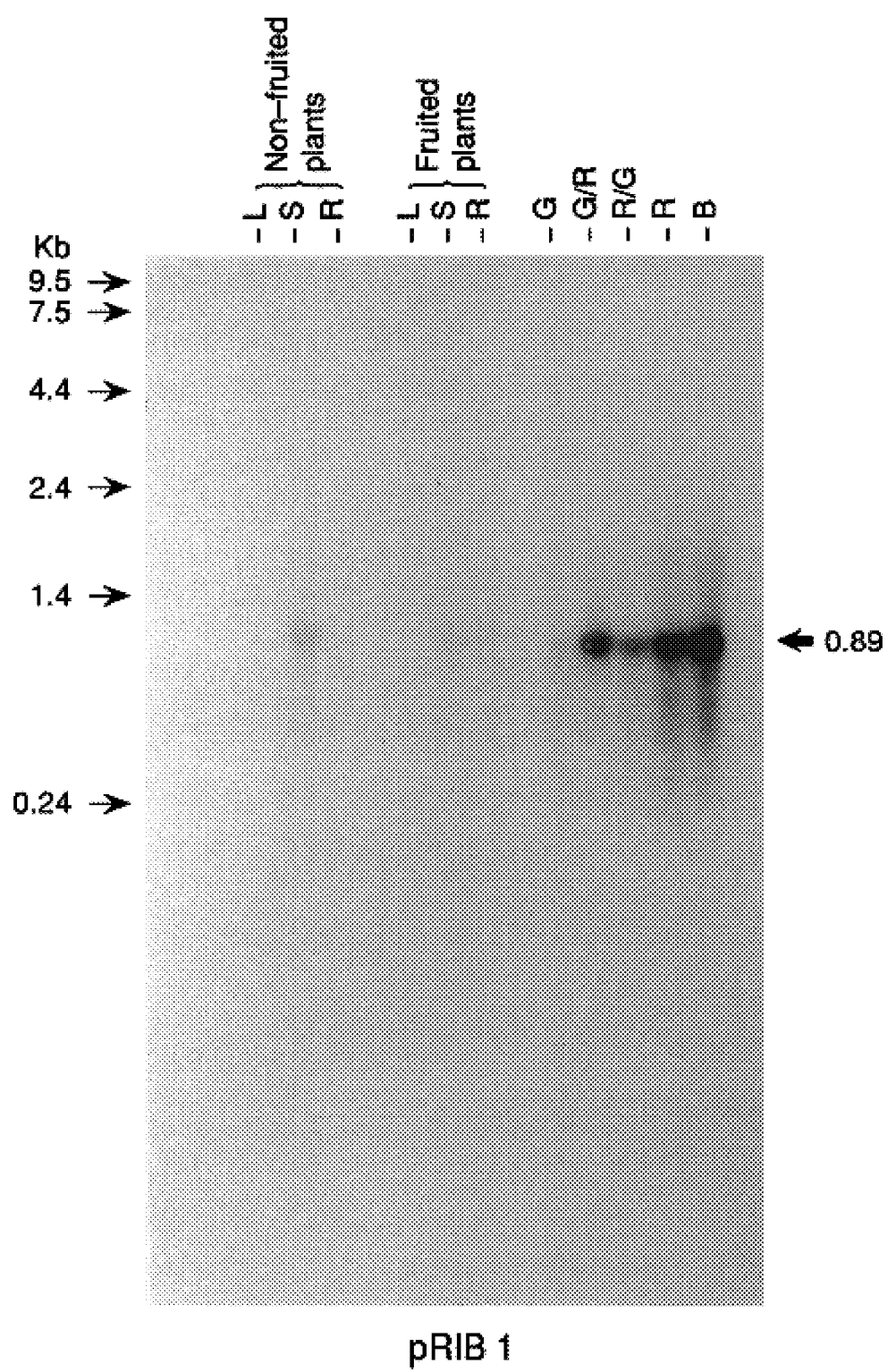
FIG. 1 shows the results of an RNA blot analysis of total RNA isolated from blackcurrant (cv Ben Alder)

Unless indicated otherwise the methods and standard techniques used below are as given in Sambrook et al (1989).

Example 1
Pigment and Respiratory Analysis
1.1 Plant material

Fruit, leaves and stems were harvested from blackcurrant (*Ribes nigrum* L. cv. Ben Alder) plants grown in experimental field plots at the Scottish Crop Research Institute, Invergowrie, Dundee, UK. Blackcurrant tissues were harvested and frozen immediately in liquid nitrogen. Thereafter, tissues were stored at −80° C. prior to analysis. Roots, leaves and stems were harvested from either one year old plants that had not yet borne fruit or from two-year-old plants that were producing fruit. Fruits were harvested at five stages of ripening as determined by fruit colour (designated green, green/red, red/green, red and black).

1.2 Determination of Fruit Anthocyanin Content

Blackcurrant fruit (0.5 g FWt) was ground to fine powder in liquid nitrogen and extracted with 1 ml of methanol containing 1% (v/v) trifluroacetic acid. After centrifugation (16000 g, 10 min) the pellet was re-extracted with a further 1 ml of methanol/trifluroacetic acid. The absorbance of the combined extracts at 518 nm was determined spectrophotometrically. Anthocyanin concentration in the extracts was estimated by comparison with a standard curve produced using the artificial pigment, amaranth (trisodium 3-hydroxy-4-(4-sulphonato-1-naphthylazo)naphthalene-2,7-disulphonate).

1.3 Ethylene and $CO_2$ Determinations

The rate of ethylene and $CO_2$ evolution from harvested blackcurrant fruit was determined using a Hewlett Packard 5890A gas chromatograph. Blackcurrant fruit were placed in gas-tight jars and incubated at 15° C. for up to 24 h. Sampling was carried out using a gas-tight syringe. For $CO_2$ determinations, the gas chromatograph was fitted with a thermal conductivity detector and a Porapak Q column (2 mm internal diameter, 1.85 M length) maintained at 50° C. A flow rate of 20 $cm^3$ $min^{-1}$ was set for the carrier gas (helium) and the peaks were integrated on a Spectra-Physics integrator (San Jose, Calif., USA). The chromatograph was calibrated with injections of 1 ml samples of 1% $CO_2$ (Phase Separations Ltd, Clwyd, Wales, UK). For ethylene measurements, the gas chromatograph was fitted with a flame ionization detector and a Porapak R column (2 mm internal diameter, 1.85 M length) maintained at 80° C. The flow rate of carrier gas (helium) was 50 $cm^3$ $min^{-1}$ and the system was calibrated by injecting 1 ml samples of ethylene gas at a concentration of 91 ppm (Phase Separations Ltd, Clwyd, Wales, UK). All peaks were integrated using a Hewlett-Packard 3390A integrator.

Results
Rate of Ethylene and Carbon Dioxide Production by Blackcurrant Fruit

Very low levels of ethylene were produced by fruit from all stages of ripening (the level of ethylene from green, green/red and red/green fruit was below the detection limit of the gas chromatograph (approximately 0.1 ppm)). As an indication of the rate of respiration of the ripening fruit, the rate of $CO_2$ production was determined. There was no burst in respiration rate as the fruit ripened. In fact, the highest rate of $CO_2$ production was produced by green fruit. In the later ripening stages, the level was approximately 20% lower than in the green fruit and remained constant as the fruit ripened from the green/red to the black stage.

Example 2
RNA Extraction

RNA was extracted from Ben Alder fruit at five ripening stages, and from leaf, root and stem material from fruited and non-fruited Ben Alder plants. Glassware was baked at 180° C. for 12 h and plasticware and Miracloth (Calbiochem) were autoclaved prior to use. Solutions were prepared from stocks by dilution in sterile DEPC-treated (diethyl pyrocarbonate) distilled water before autoclaving. Unless otherwise stated, the procedures were carried out at 4° C. Freshly harvested berries were weighed into 50 g portions and stored on ice. Leaf, root and stem material was harvested, rapidly frozen in liquid nitrogen and stored at −80° C. until required. Fruit (50 g) was pulped with 100 ml of homogenisation buffer (200 mM Tris.HCl pH 8.5, 300 mM LiCl, 10 mM $Na_2EDTA$, 1% (w/v) sodium deoxycholate, 1.5% (w/v) sodium dodecyl sulphate, 8.5% (w/v) insoluble polyvinylpolypyrrolidone (PVPP), 1% (v/v) Nonidet P40, 1 mM aurintricarboxylic acid, 5 mM thiourea, and 10 mM dithiothreitol (the last three components were added as solids after autoclaving)) in a domestic coffee grinder for 45 s. Leaves, roots and stems were ground to a fine powder in a sterile pestle and mortar, with a little sand (previously baked at 180° C. for 12 h) in liquid nitrogen and 5 vol of homogenisation buffer (containing 4% PVPP instead of 8.5%) was added per gramme of tissue. The viscous material was poured into sterile 50 ml tubes. If not required for immediate use, the fruit pulp was frozen in liquid nitrogen and stored at −80° C.

Frozen fruit pulp was defrosted rapidly in a microwave oven prior to use in the extraction. To proceed with the extraction, the homogenate was diluted 1:1 with sterile water and mixed well. 20 ml of diluted homogenate was placed in a 50 ml Oak Ridge-type centrifuge tube containing 15 ml homogenisation buffer and shaken. The tubes were placed in a waterbath at 65° C. for 10 min, with occasional mixing, and then centrifuged at 12,000×g for 30 min at 4° C. The supernatant was filtered through two layers of Miracloth and collected in an Oak Ridge-type centrifuge tube and solid CsCl was dissolved in the supernatant to a final concentration of 0.2 g CsCl per ml of filtered extract. The extract was gently layered onto a 10 ml cushion of 5.7 M CsCl containing 10 mM Tris.HCl pH 7.5 and 10 mM $Na_2EDTA$, in a Beckman 50 ml ultracentrifuge tube and centrifuged at 100,000×g for 20 h at 20° C. After centrifugation, the supernatant was carefully removed with a syringe and discarded. The RNA pellet remained at the bottom of the tube.

The pellet was washed with 5 ml of ice-cold 70% ethanol, centrifuged at 10,000×g for 10 min at 4° C. and the tubes inverted to allow the pellet to dry. The RNA was resuspended in a total of 1 ml of sterile distilled water and transferred to a sterile microfuge tube. 200 μl of 3 M LiCl (0.5 M final concentration) and 2.5 ml of 95% ethanol was added to precipitate the RNA (overnight at −20° C.).

RNA was recovered by centrifugation at 16,000×g for 30 min at 4° C., and the pellet was washed three times with 0.5 ml 2.5 M sodium acetate (pH 5.5). Following centrifugation at 16,000×g for 15 min at 4° C. and removal of the supernatant, the pellet was resuspended in 100 μl of sterile distilled water. Ethanol (95%) was slowly added to a final concentration of 30% (v/v) of the total and the tube vortexed briefly. After centrifugation at 16,000×g for 2 min at 4° C. the supernatant containing the RNA was transferred to a fresh microfuge tube and precipitated by the addition of 0.1 vol sodium acetate pH 5.2 and 3 vol ethanol and incubation at −20° C. overnight. The RNA was recovered by centrifugation at 16,000 ×g for 30 min at 4° C., the pellet washed in 0.5 ml 70% ethanol and allowed to dry before it was suspended in sterile water.

Example 3

RNA Analysis

Total RNA was extracted from blackcurrant tissues as described above in Example 2. Steady-state transcript levels were determined by RNA blot analysis. Total RNA (15 μg/track) was separated electrophoretically under denaturing conditions and transferred by capillary action onto Hybond-N membranes (Amersham) as recommended by the manufacturer. Blots were probed with $^{32}$P labelled cDNA inserts isolated from cDNA clones following restriction endonuclease digestion. Inserts were separated by electrophoresis through agarose gels and purified by electroelution. After hybridisation for 16–24 h at 42° C. in 50% formamide, filters were washed sequentially in 2×SSC, 0.5% SDS followed by 2×SSC, 0.1% SDS and then 0.1%×SSC, 0.1% SDS for 20 min per wash at 52° C. prior to exposure to X-ray film at −70° C. for between 24 and 96 h. Transcript size was determined by comparison of electrophoretic mobility with RNA markers of known sizes (Life Technologies). The intensity of the hybridisation signal was determined by densitometry using a Millipore Bio-Imager (Millipore, Mich., USA).

FIG. 1 shows the results of one RNA blot analysis. Total RNA was isolated from blackcurrant (cv. Ben Alder) leaves (L), stems (S) and roots (R) from plants that had borne fruit and from those that had not, and from fruit at five ripening stages (G=green; GR=green/red; R/G=red/green; R=red; B=black). Total RNA (20 μg per lane) was analysed by electrophoresis through a 1.2% denaturing agarose gel, blotted onto nylon membrane and hybridised with a labelled probe prepared to pRIB1, using standard techniques.

Example 4 cDNA Clone Isolation and Analysis

A cDNA library was constructed from polyadenylated RNA (7 μg) extracted from green/red blackcurrant fruit. Polyadenylated RNA was prepared by affinity chromatography using oligo d(T) cellulose (Life Technologies). Double stranded cDNA was synthesised and directionally ligated into EcoRI/XhoI digested lambda Zap arms using a Uni-Zap XR vector kit (Stratagene). The library was packaged using an in vitro kit (Stratagene) and plated on the XL1-Blue strain of *E. coli* (Stratagene).

Differential Gene Expression During Ripening

The cDNA library was screened with $^{32}$P labelled cDNA from green fruit and green/red fruit. By differentially screening a total of 10,000 plaques, five were found to be differentially expressed between these stages. The in vivo excision protocol of Stratagene with the R408 helper phage was used to rescue putative ripening-related cDNAs in pBluescript SK (−) plasmids. The plasmids were purified using Qiagen columns (Qiagen Ltd., Dorking, UK). Steady-state expression levels of the corresponding genes (designated RIB1, RIB3, RIB5, RIB6 and RIB7) were determined by RNA blot analysis. The intensities of the hybridisation signals were determined by densitometry. For all clones, very low or negligible levels of expression could be detected in the green fruit and the highest levels of expression were detected in black, fully ripe fruit. In the quantitative densitometric analysis therefore, steady-state transcript levels are expressed relative to the level in black fruit. In order to demonstrate equal loading and transfer of RNA during this analysis, filters were stripped and hybridised with a potato 25S ribosomal RNA probe. An equivalent hybridisation signal was detected for RNA extracted from tissue at all stages (data not shown).

Expression in other Blackcurrant Tissues

Steady-state expression levels of the RIB genes were also determined in leaves, stems and roots of blackcurrant plants that had borne fruit and from those that had not. A variety of expression patterns were observed. For example, the expression of RIB1 and RIB7 was confined largely to fruit. RIB3, RIB5 and RIB 6 expression however was less specific to fruit and relatively high expression levels could be detected in some of the other plant tissues that were tested. The expression level of some of the clones was different depending on whether the blackcurrant plants had produced fruit or not. For example, the expression level of RIB5 was higher in plants that had never produced fruit compared with tissues from plants that had.

The clone pRIB1 hybridised to cDNA probes prepared from mRNA from ripe fruit but not to cDNA probes prepared from green, unripe fruit. Using the cloned pRIB 1 cDNA as a probe, a blackcurrant (cv. Ben Alder) genomic library constructed in λ Fix II (custom synthesised by Stratagene Ltd, Cambridge, UK) was screened using standard techniques (Sambrook et al., 1989). A genomic clone corresponding to the cDNA clone was isolated and the blackcurrant RIB1 genomic clone was plaque purified. DNA was prepared and fragments subcloned into plasmid vectors by standard procedures (Sambrook et al., 1989). The RIB1 genomic clone contained an insert of 18 kilobase pairs (kbp) from which the relevant sub-fragments were cloned into plasmid vectors. One subclone contains approximately 3 kbp of gene sequence (two exons and one intron) including approximately 1.8 kbp of 5' flanking sequence which contains the blackcurrant RIB1 promoter region.

RNA blot analysis (Sambrook et al., 1989) of blackcurrant tissues indicates that the gene is highly expressed in ripe blackcurrant fruit and expressed at negligible levels in other tissues of the blackcurrant plant (FIG. 1). Therefore this promoter region will be suitable to drive the expression of any piece of DNA cloned downstream of it (that is, following the 3' terminus of the promoter region) in ripening fruit but not in unripe fruit.

A positive genomic clone corresponding to the RIB 7 cDNA (RIB 7) was isolated from the blackcurrant (*Ribes nigrum* L., cv. Ben Alder) genomic library and sub-cloned using the same techniques as for RIB 1. Two adjacent sub-clones (as determined by PCR) were sequenced and the RIB7 gene is contained within this sequence.

DNA Sequence Analysis

Plasmid DNA for sequencing was prepared using Qiagen columns. DNA sequence was obtained from both strands of alkaline denatured plasmid by manual dideoxysequencing using Sequenase version 2.0 (United States Biochemical Corporation) or by automated sequencing using an AB1 373 automated sequencer. DNA sequences were compiled and compared using the sequence analysis software and databases available on the SEQNET Computational Molecular Biology facility at SERC Daresbury Laboratory, UK.

Genomic DNA Isolation and Southern Analysis

Genomic DNA was isolated from the leaves of three blackcurrant cultivars (Ben Alder, Ben Sarek and Baldwin), Tayberries (*Rubus loganobaccus*) and raspberries (*Rubus idaeus* cv. Glen Moy). Leaves (1 g FWt) were ground to a fine powder in liquid nitrogen. 2.5 ml buffer containing 2% (w/v) CTAB, 100 mM Tris.HCl pH 8.0, 1.4 M NaCl, 20 mM $Na_2EDTA$, 0.1% (w/v) DTT at 65° C. was added and mixed gently prior to the addition of 0.1 g Polyclar AT (BDH). After a 30 min incubation at 65° C., 7.5 ml of chloroform:isoamyl alcohol (24:1 [v/v] ) was added and gently mixed. Following centrifugation (5000 g, 5 min) the aqueous phase was removed and mixed with an equal volume of propan-2-ol. After a 15 min incubation at room temperature, nucleic acids were pelleted by centrifugation (10000 g, 15 min). The air-dried pellet was resuspended in 0.85 ml water before the addition of 50 µl 1M KAc, pH 5.5, 20 µl of 0.5 M $Na_2EDTA$, 50 µl Caylase (10 mg/ml [Cayla, Toulouse, France]), 1 µl RNase A (10 mg/ml [Sigma]) and 29 µl water. The mixture was incubated for 14 h at 37° C. 50 µl of 1M Tris.HCl (pH 8.0) was then added to the solution prior to extraction with one volume of chloroform:IAA (24:1 [v/v]). Genomic DNA was precipitated with three volumes of ethanol, washed with 70% ethanol, air dried and finally resuspended in TE buffer (pH 8.0).

Figure 2:
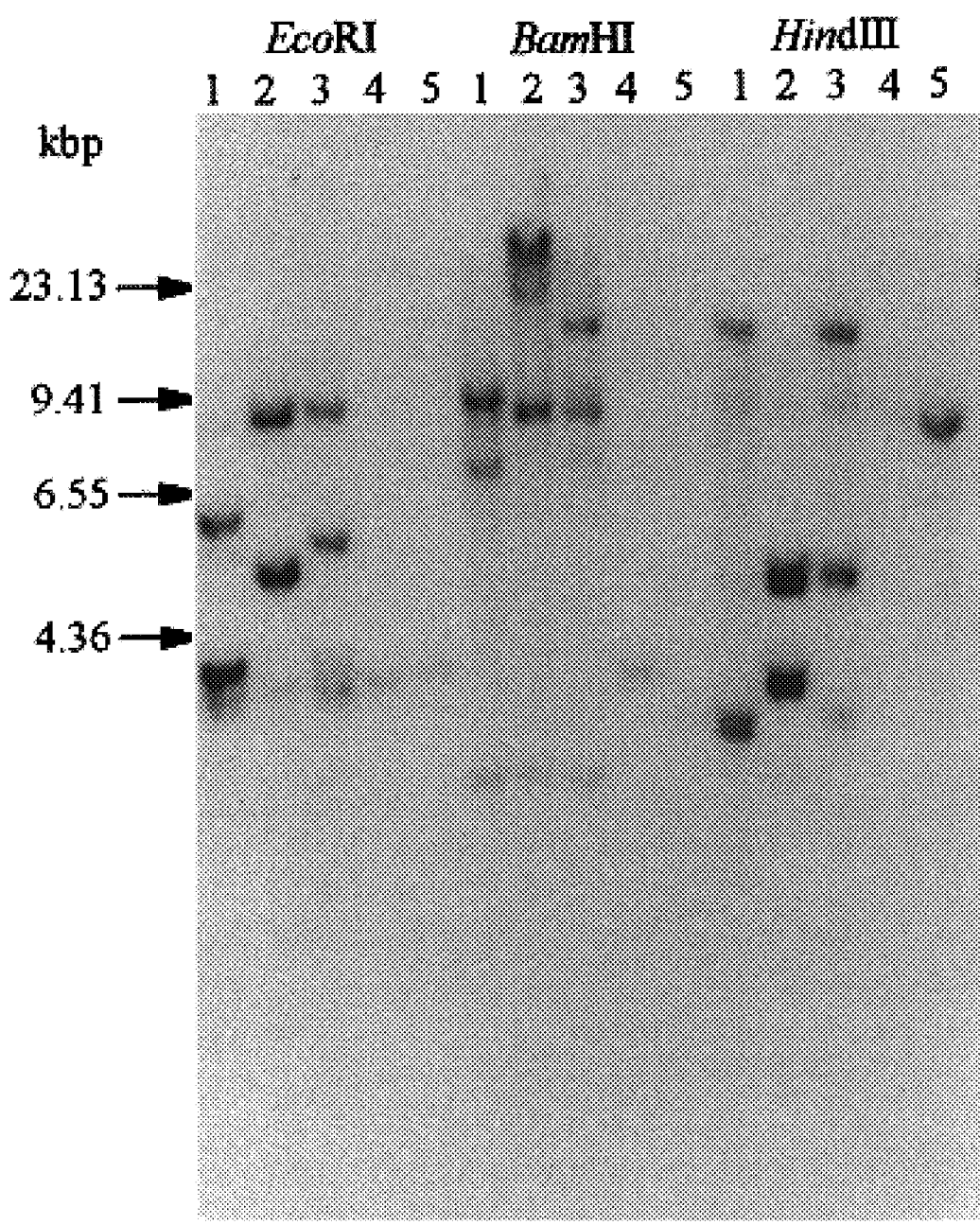
FIG. 2 shows the results of a DNA blot analysis.

5 µg of each DNA sample was digested separately with the restriction endonucleases EcoRI, BamHI and HindIII and resolved by electrophoresis on 0.8% (w/v) agarose gels. DNA was transferred under vacuum to Hybond N membranes (Amersham) and hybridised with the $^{32}P$ labelled inserts of the pRIB 1 clone, prepared as above. Filters were washed at high stringency (0.1×SSC, 0.1% SDS at 65° C.) and exposed to X-ray film for 24–72 h at −70° C. with intensifying screens. FIG. 2 shows the results of one DNA blot analysis : Genomic DNA (5 µg per lane) from the blackcurrant cultivars Ben Alder (lane 1), Ben Sarek (lane 2) and Baldwin (lane 3), Tayberry (lane 4) and the raspberry cultivar Glen Moy (lane 5), was digested with either of the restriction endonucleases EcoRI, BamHI or HindIII, and fractionated on an 0.8% (w/v) agarose gel. The DNA was blotted onto nylon membrane hybridised with a labelled probe prepared to pRIB1, using standard techniques (Sambrook et al., 1989).

Results

Sequence Analysis of the pRIB Clones pRIB 1

The size of the insert in pRIB1 is 882 base pairs, similar to that expected from the estimate of transcript size. A potential long open reading frame was identified from nucleotide position 3 to the TAA termination codon at position 489. A translation start codon is not present in this ORF indicating that the 5' portion of the cDNA is absent. A polyadenylation signal was identified in the cDNA sequence. Comparison of the deduced amino acid sequence of this ORF and the nucleotide sequence of the cDNA did not reveal any significant sequence similarity to other sequences in the European Molecular Biology Laboratory (EMBL) database of gene sequences.

When compared with the SwissProt protein database using the 'Blitz' programme (MPsrch programme, Biocomputing Research Unit, University of Edinburgh, UK) the putative amino acid sequence shows similarity (% 50.9% similarity, 36.9% identity) to a cDNA encoding a protein isolated from kiwifruit (Ledger and Gardner,1994). The steady state level of the kiwifruit transcript increases during fruit development, but declines during ripening. This is in contrast to the expression of the RIB1 gene in blackcurrant fruit where the steady state transcript level increases during the ripening period. Importantly, like the blackcurrant transcript, the kiwifruit gene is expressed almost entirely in the fruit.

pRIB 3

The ORF present in pRIB3 encodes a polypeptide which shares a high degree of sequence similarity with group one metallothioneins. The most similar metallothionein protein to the blackcurrant deduced sequence was from kiwifruit (79% similarity, 67% identity). Typical of metallothioneins, the putative blackcurrant polypeptide has a low $M_r$ value ($M_r$ 6808) and is acidic (pI 4.56). Metallothioneins also contain characteristic cysteine rich domains and the arrangement of these regions in blackcurrant and in a kiwifruit metallothionein is highly conserved. There are two Cys pairs in the N-terminal domain and three Cys pairs in the C-terminal domain separated by a hydrophobic domain. This organisation has also been observed in putative metallothioneins isolated from rice and Arabidopsis but differs from some plant sequences where there are three Cys pairs in the N-terminal domain.

pRIB 5

A long ORF was also identified in the pRIB5 cDNA sequence, extending from the nucleotide in position 3 to the termination codon in position 777. A methionine initiation codon was not present in this ORF indicating that the cDNA was not full length. Searches of the EMBL database with the deduced amino acid sequence of this ORF and also with the nucleotide sequence did not reveal any significant similarities to known sequences. The putative amino acid sequence encoded by pRIB5 does not show significant similarity to other amino acid sequences in the SwissProt database.

p RIB 6 pRIB6 encodes the C-terminal portion of a polypeptide that shares sequence similarity with the cysteine proteinase family. This group of proteins includes actinidin from kiwifruit, papain from papaya and bromelain from pineapple. The putative protein encoded by pRIB6 shows most similarity to a cysteine proteinase precursor from *Arabidopsis thaliana* (74% similarity, 60% identity), the expression of which is induced by high salt conditions. Five of the highly conserved residues found in or near the active site of all cysteine proteases are present in the blackcurrant sequence.

pRIB7.

pRIB7 contains a long ORF extending from a putative methionine initiation codon at nucleotide 29 to a TAA termination codon at position 860. The ORF encodes a protein of $M_r$ 29,215 and a pI of 7.9. However, a common poly(A)+addition sequence is not present. The pRIB7 ORF was most similar to the yeast mitochondrial protein MRS4, a mitochondrial RNA splicing protein (62% similar and 42% identical at the amino acid level). Hydropathy plots have shown that the MRS4 protein contains potential membrane spanning domains and analysis of the pRIB7 ORF sequence shows that this may also be the case for the blackcurrant polypeptide. The MRS4 protein contains three repeated amino acid sequences of approximately 100 residues and a characteristic highly conserved domain. Such sequence motifs are also seen in a number of mitochondrial carrier proteins.

RIB 7

The 5150 nucleotide sequence contains a 'TATA box' element at nucleotide 3041 and a putative ATG translational start codon at position 3156. This translational start codon is in the context TTTTCAATGGCG and matches the optimal context consensus sequence (NNANNATGGCT), where N is any nucleotide) proposed by Heidecker and Messing (1986) in all but two positions (these are underlined).

By comparison with the cDNA sequence, the RIB 7 gene contains two exons and one intron. The 454 nucleotide intron is located between bases 3927 and 4381. On the basis of the translational start codon being located at position 3156, the putative polypeptide encoded by the RIB 7 gene is composed of 328 amino acids. The deduced amino acid sequence has been compared with others in the SwissProt database and is most similar to a mitochondrial RNA splicing protein (MRS4: Accession number P32500) from yeast (60.3% similarity and 40.3% identity).

Southern Analysis

Southern blots of genomic DNA from R. nigrum (cvs Ben Alder, Ben Sarek and Baldwin), R. loganobaccus (Tayberry) and R. idaeus (cv Glen Moy), were hybridised with probes from the RIB genes. Generally, with all these probes, a small number (2 to 4) of hybridising bands were detected by Southern analysis when the genomic DNA was digested with BamHI, EcoRI or HindIII. This indicates that the RIB genes are present in low copy number in the genomes of these diploid species. Blots probed with RIB3 and RIB5 showed that these or similar sequences are not present in the genomes of raspberry and Tayberry as no hybridising bands could be detected on the Southern blots (data not shown). As a control, these blots were stripped and re-probed with a potato P-tubulin probe which gave multiple hybridisation signals with genomic DNA from all the samples that were probed (data not shown).

Discussion

On the basis of respiration measurements, blackcurrants do not exhibit a typical climacteric pattern of ripening. Additionally, the large increase in ethylene evolution that commonly accompanies the respiratory climacteric was not detected. Compared with the rate of ethylene production from ripening avocado fruit (internal ethylene levels increase 1000-fold between the pre-climacteric and climacteric peak) the amount of ethylene produced by blackcurrant fruit was very low. It is not clear which plant growth regulators trigger ripening processes in blackcurrant fruit.

Irrespective of the plant growth regulators that control ripening in blackcurrant fruit, until now, none of the genes that are differentially expressed during fruit ripening have been isolated. A cDNA library constructed from the green/red stage of ripening was differentially screened with probes from this stage and from green fruit, since genes that are differentially expressed as anthocyanin accumulation commences are good candidates for having an important role in this and other ripening processes. In fact the expression of all five genes corresponding to the isolated cDNAs, continued to increase as ripening progresses and reached a maximum steady-state level in fully ripe, black fruit (FIG. 1). The expression of these genes showed varying degrees of fruit specificity. RIB1 and RIB7 were expressed only at very low levels in non-fruit tissues. The promoters driving the expression of these two genes therefore are good candidates for being fruit specific promoters and therefore suitable for use in manipulating ripening processes in transgenic fruit. RIB3, RIBS and RIB6 were also expressed in roots leaves and stems. RIB3 exhibited a markedly different expression pattern in stems and roots from plants that had not borne fruit (no detectable expression) compared with plants that had (relatively high steady-state transcript levels). It seems likely that the expression of these genes is highly regulated in a tissue- and developmental-stage specific manner.

In order to determine the copy number and occurrence of the RIB genes in other soft fruit species, Southern blot analyses were performed. Of the five clones isolated from the cDNA library, three of them, pRIB1, pRIB6 and pRIB7 hybridised to DNA from three blackcurrant cultivars, Tayberry and red raspberry. These clones may represent genes that occur widely in soft fruit species. Interestingly, in Southern blots probed with pRIB3 and pRIBS, hybridising bands were only present in lanes containing blackcurrant DNA, suggesting these genes and related sequences are absent in other soft fruit species.

It was possible to identify tentatively three of the blackcurrant sequences based on similarity searches of databases. Sequences similar to pRIB3, encoding a metallothionein-like protein and pRIB6, encoding a cysteine proteinase have been found previously to be expressed in many plant species. A number of highly conserved amino acid residues, essential for protease activity, are present in the putative blackcurrant sequence.

The pRIB3 ORF has strong sequence similarity to a number of metallothionein-like proteins that have been isolated previously from plants. It is interesting, that of these proteins, the most similar to the pRIB3 sequence, was isolated from the ripening fruit of kiwifruit. Like pRIB3, high steady-state transcript levels of the kiwifruit gene were detected in ripe fruit. In animals, metallothioneins function to maintain metal ion homeostasis and are involved in metal ion detoxification. Additionally they may provide protection against oxidative stress. Although no similar functions have yet been demonstrated for plant metallothioneins, it is possible that they have similar roles. Indeed plant metallothionein-like proteins have been shown to bind cadmium and copper. However it is unclear at the moment, why the steady-state level of the metallothionein-like protein specific transcript increases in ripe fruit. It is interesting that DNA sequences hybridising to the RIB3 probe on the Southern blot were only present in blackcurrant, and not in raspberry or Tayberry.

pRIB7 was most significantly similar to a gene that has not been previously found to be expressed in plants, the yeast MRS4 gene. This nuclear gene encodes a mitochondrial RNA splicing protein. Although most similar to the MRS4 gene product, the pRIB7 ORF shares some sequence motifs with a number of mitochondrial carrier proteins such as the phosphate carrier protein and the ADP/ATP translocase. The mitochondrial carrier family is characterised by three tandem repeats of a domain of approximately 100 residues, and a highly conserved region within the repeated domain serves as a signature pattern. This consensus pattern (P-Xaa-[D,E]-Xaa [L, I, V, A, T]-[R, K]-Xaa-[L,R]-[L, I, V, M, F, Y]) is found three times in the pRIB7 ORF although one amino acid residue in the repeat in the —COOH-domain differs from this consensus pattern (Q in place of L or R). The role of the pRIB7 polypeptide therefore is unknown but it may be related to changes in solute transport across the mitochondrial membrane, reflecting changes in metabolism as fruit ripen. The pRIB1 and pRIB5 ORFs did not show any sequence similarity to known sequences in the EMBL database.

REFERENCES

Bevan, M. (1984). Nucl. Acid. Res. 12, 8177.
Callahan, H., Morgens, P and Walton, E (1989). Hortsci. 24, 356–358
Fromm, M. E., Taylor, L. P. & Walbot, V. (1985). Proc. Natl. Acad. Sci. USA 82, 5824–8.
Heidecker, G. and Messing, J. (1986). Ann. Review of Plant Physiology, 37, 439–466.

Klein, T. M., Wolf, E. D., Wu, R. & Sandford, J. C. (1987). *Nature* 327, 70–73.

Lay-Yee, M., Dellapenna, D. amd Ross, G. S. (1990). *Plant Physiol.* 94, 850–853

Ledger, S. E. and Gardner, R. C. (1994) *Plant Mol. Biol.* 25, 877–886

Martin, C., Prescott, A., Mackay, S., Bartlett, J. & Vrijlandt, E. (1991). *Plant J.* 1, 37–49.

Sambrook, J., Fritsch, E. F. & Maniatis, T. (1989). Molecular Cloning: A Laboratory Manual, 2nd Edn. Cold Spring Harbor Laboratory Press.

Schuch, W., Kanczler, J., Robertson, D., Hobson, G, Tucker, G, Grierson, D, Bright, S, Bird, C. *Hortsci* 26, 1517–1520. (1991).

Tesniere, C. & Vayda, M. E. (1991). *Plant Mol. Biol. Reptr.* 9, 242–251.

What is claimed is:

1. An isolated DNA comprising a promoter that drives fruit specific expression in blackcurrant wherein the DNA hybridizes under conditions of high stringency to a DNA consisting of the nucleic acid bases set forth in a member selected from the group consisting of the nucleic acid bases set forth in SEQ ID NO: 11 and nucleic acid bases 1 to 3156 set forth in SEQ ID NO: 14.

2. The isolated DNA of claim 1 wherein the DNA comprises the nucleic acid bases set forth in SEQ ID NO: 11.

3. The isolated DNA of claim 2 wherein the DNA comprises nucleic acid bases 1 to 3156 of SEQ ID NO: 14.

4. An isolated DNA that is the full complement of the DNA of claim 1.

5. A vector comprising the isolated DNA as claimed in claim 1.

6. A method to control the expression of one or more genes in non-climacteric fruit comprising:
   a) transforming a plant cell with the vector of claim 5; and
   b) growing the plant cell under conditions wherein the promoter drives expression of the one or more genes.

7. The method according to claim 6 wherein the non-climacteric fruit is blackcurrant.

8. A transgenic plant cell comprising the DNA of claim 1.

9. A transgenic plant comprising the cell of claim 8 and transgenic descendants thereof.

10. The transgenic plant according to claim 9 wherein the plant is a blackcurrant.

11. A transgenic plant cell or plant transformed by a vector according to claim 5.

12. A transgenic seed derived from the plant of claim 10.

* * * * *